(12) United States Patent
Strauss et al.

(10) Patent No.: US 8,025,694 B2
(45) Date of Patent: Sep. 27, 2011

(54) MODULAR VASCULAR PROSTHESIS AND METHODS OF USE

(75) Inventors: David P. Strauss, Temecula, CA (US); Michael R. Bialas, Temecula, CA (US); Duane DeMore, Temecula, CA (US); Robert Barbier, Perris, CA (US); Rainer Bregulla, Balingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 326 days.

(21) Appl. No.: 11/962,463

(22) Filed: Dec. 21, 2007

(65) Prior Publication Data
US 2009/0005848 A1 Jan. 1, 2009

Related U.S. Application Data

(63) Continuation-in-part of application No. 11/067,090, filed on Feb. 25, 2005.

(51) Int. Cl.
*A61F 2/86* (2006.01)
(52) U.S. Cl. .................................... 623/1.16
(58) Field of Classification Search ........ 623/1.15–1.18, 623/1.38
See application file for complete search history.

(56) References Cited

U.S. PATENT DOCUMENTS

| | | |
|---|---|---|
| 4,580,568 A | 4/1986 | Gianturco |
| 4,739,762 A | 4/1988 | Palmaz |
| 5,632,771 A | 5/1997 | Boatman et al. |
| 5,741,327 A | 4/1998 | Frantzen |
| 5,824,037 A | 10/1998 | Fogarty et al. |
| 5,824,046 A | 10/1998 | Smith et al. |
| 6,015,815 A | 1/2000 | Mollison |
| 6,048,361 A | 4/2000 | Von Oepen |
| 6,129,755 A | 10/2000 | Mathis et al. |
| 6,187,036 B1 | 2/2001 | Shaolian et al. |
| 6,231,598 B1 | 5/2001 | Berry et al. |
| 6,293,966 B1 | 9/2001 | Frantzen |
| 6,336,937 B1 | 1/2002 | Vonesh et al. |
| 6,409,754 B1 | 6/2002 | Smith et al. |
| 6,503,271 B2 | 1/2003 | Duerig et al. |
| 6,540,777 B2 | 4/2003 | Stenzel |
| 6,562,067 B2 | 5/2003 | Mathis |
| 6,585,764 B2 | 7/2003 | Wright et al. |
| 6,599,314 B2 | 7/2003 | Mathis |
| 6,814,746 B2 | 11/2004 | Thompson et al. |
| 6,945,995 B2 | 9/2005 | Nicholas |
| 7,235,093 B2 | 6/2007 | Gregorich |
| 2001/0027340 A1 | 10/2001 | Wright et al. |
| 2001/0053929 A1 | 12/2001 | Vonesh et al. |

(Continued)

FOREIGN PATENT DOCUMENTS
DE 203 08 672 9/2003
(Continued)

OTHER PUBLICATIONS

U.S. Appl. No. 11/067,090, filed Jul. 12, 2007, Office Action.
(Continued)

*Primary Examiner* — Ryan J Severson
(74) *Attorney, Agent, or Firm* — Workman Nydegger

(57) ABSTRACT

The present invention relates a vascular prosthesis and related assembly methods that includes a plurality of modular segments inter-engaged by flexible, and preferably lockable, inter-engageable elements forming joints or other connector areas. The segments may have a number of different mechanical properties and may be assembled by the clinician, through mechanical or chemical joining, to customize the prosthesis for a specific patient or application.

26 Claims, 13 Drawing Sheets

U.S. PATENT DOCUMENTS

| | | | |
|---|---|---|---|
| 2002/0010507 A1 | 1/2002 | Ehr et al. | |
| 2002/0111671 A1 | 8/2002 | Stenzel | |
| 2002/0120327 A1 | 8/2002 | Cox et al. | |
| 2002/0188343 A1 | 12/2002 | Mathis | |
| 2002/0188347 A1 | 12/2002 | Mathis | |
| 2003/0135265 A1* | 7/2003 | Stinson | 623/1.16 |
| 2003/0135266 A1* | 7/2003 | Chew et al. | 623/1.16 |
| 2004/0044398 A1 | 3/2004 | Nicholas | |
| 2004/0093077 A1 | 5/2004 | White et al. | |
| 2004/0236406 A1 | 11/2004 | Gregorich | |
| 2005/0182475 A1 | 8/2005 | Jen et al. | |
| 2006/0030932 A1 | 2/2006 | Kantor et al. | |
| 2006/0069424 A1* | 3/2006 | Acosta et al. | 623/1.12 |
| 2006/0195175 A1 | 8/2006 | Gregulla | |

FOREIGN PATENT DOCUMENTS

| | | |
|---|---|---|
| DE | 20308672 | 9/2003 |
| WO | 00/15151 | 3/2000 |
| WO | WO 00/15151 | 3/2000 |
| WO | 03/049640 | 6/2003 |
| WO | WO 03/049640 | 6/2003 |
| WO | 03/075797 | 9/2003 |
| WO | WO 03/075797 | 9/2003 |
| WO | 2004/014256 | 2/2004 |
| WO | WO 2006/089739 | 8/2006 |

OTHER PUBLICATIONS

U.S. Appl. No. 11/067,090, filed Mar. 26, 2008, Office Action.
U.S. Appl. No. 11/067,090, filed Oct. 8, 2008, Office Action.
U.S. Appl. No. 11/067,090, filed May 13, 2009, Office Action.
U.S. Appl. No. 11/067,090, filed Nov. 23, 2009, Office Action.
U.S. Appl. No. 11/067,090, filed Apr. 29, 2010, Office Action.
U.S. Appl. No. 11/067,090, filed Oct. 25, 2010, Office Action.
U.S. Appl. No. 11/067,090, filed Apr. 14, 2011, Notice of Allowance.

* cited by examiner

FIG.11
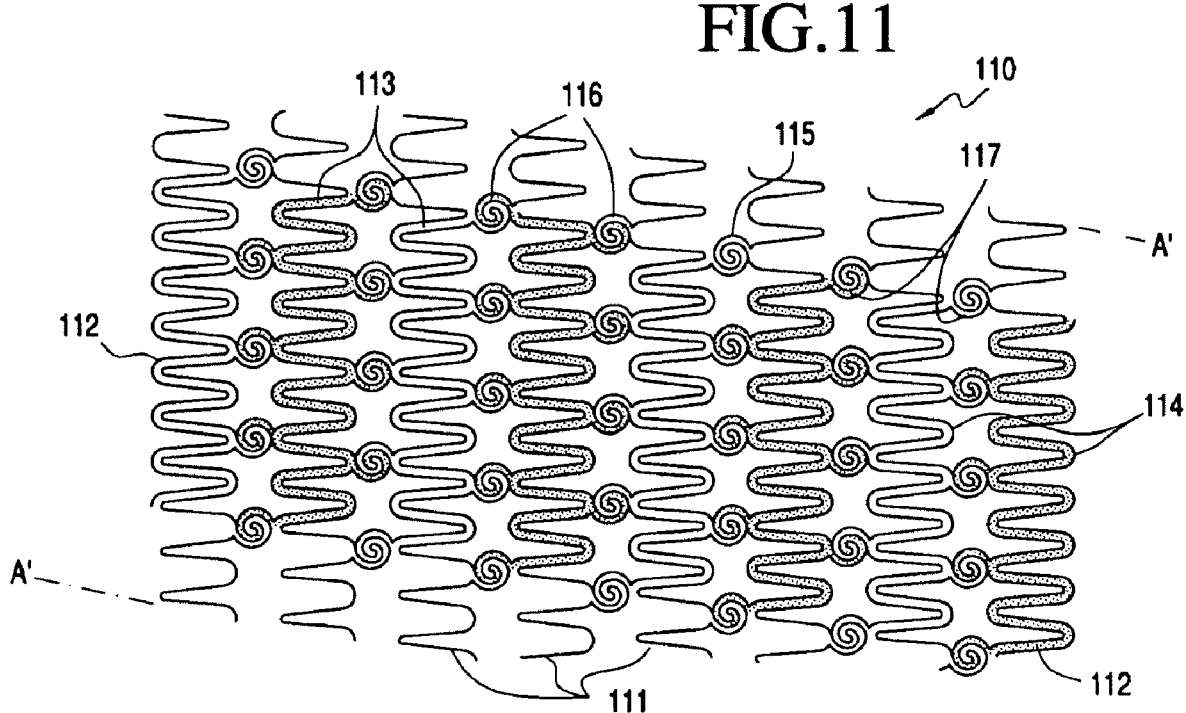
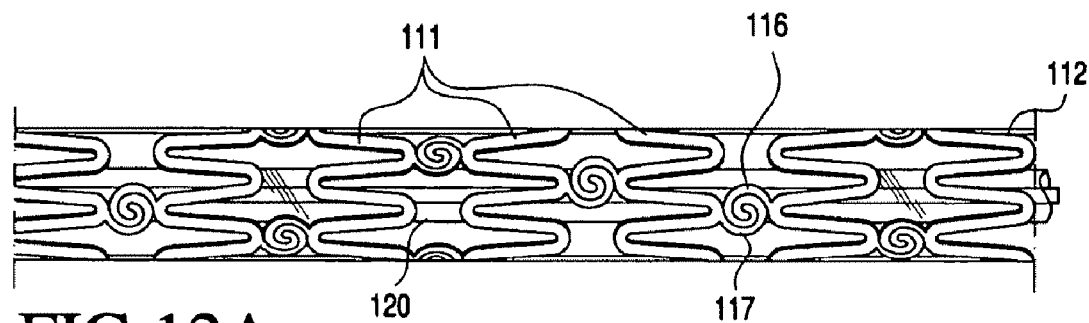
FIG.12A
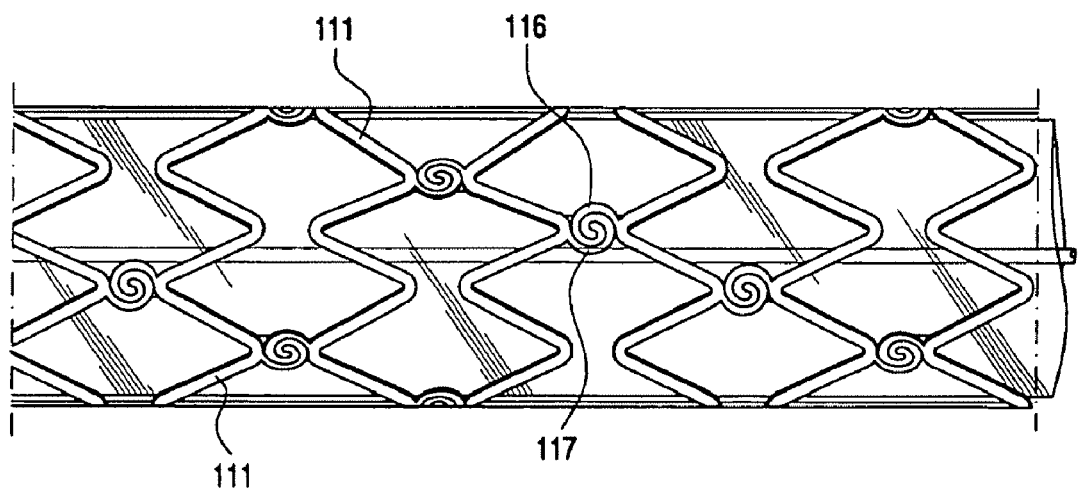
FIG.12B

MODULAR VASCULAR PROSTHESIS AND METHODS OF USE

CROSS-REFERENCE TO RELATED APPLICATIONS

The present application is a continuation-in-part of U.S. patent application Ser. No. 11/067,090, filed on Feb. 25, 2005 and published on Aug. 31, 2006 as U.S. Patent Application Publication No. 2006/0195175.

FIELD OF THE INVENTION

The present invention relates to modular vascular prostheses, such as stents, and related methods of use. More particularly, the present invention relates to vascular prostheses having a modular construction that permits the properties and length of the prosthesis to be customized for a specific patient.

BACKGROUND OF THE INVENTION

Numerous stent designs are known in the art, of which self-expanding and balloon-expandable stents are the predominant commercially available types. Self-expanding stents, such as the stents described in U.S. Pat. No. 4,580,568 to Gianturco, generally provide good crush-resistance and axially flexibility, thus permitting delivery through tortuous anatomy, but provide lower radial strength once deployed. Balloon-expandable stents, such as the stents typified by U.S. Pat. No. 4,739,762 to Palmaz, provide high radial strength, but tend to have increased axial rigidity that affects deliverability through tortuous vessels. It has therefore been a goal of many expandable stent designs to enhance axial flexibility of the stent to improve deliverability, and thus the number of potential applications for the device, while retaining an acceptable level of radial strength.

Previously known stents are generally supplied in a variety of lengths and diameters, so the clinician can select the stent most appropriate for a specific patient. Such stents typically have homogeneous properties along the length of the stent and provide limited options for customization responsive to the needs of a particular patient.

In certain applications, the best solution for a particular patient would involve a combination of the mechanical and operating properties of both balloon-expandable and self-expanding stents. Therefore, it would be desirable to provide a modular stent that permits the clinician to "mix and match" stent modules to build a stent having specific characteristics tailored for a specific patient or application.

For example, it may be desirable to provide a stent having axial modules of variable rigidity and crush-resistance, such as for use in the carotid arteries. Due to the generally exposed nature of these arteries in the region of the neck, situations have been reported where balloon-expandable stents have been subjected to partial crushing. On the other hand, self-expanding stents are susceptible to migration. Therefore, it would be desirable in certain applications to provide a stent having a resilient, self-expanding central portion and balloon-expandable end regions that permit the stent to be anchored in position.

The ability to vary the mechanical properties of the stent also would permit a stent to include non-metallic components, such as biodegradable or bioabsorbable segments. This ability might prove particularly advantageous where it is desired to deliver a predetermined dose of drug to via drug-eluting segments, for example, by incorporating a specified number of drug-eluting segments into the prosthesis that eventually dissolve in the fluid stream through the vessel.

As yet another example, U.S. Pat. No. 6,048,361 to Von Oepen describes a stent designed for use in bifurcated vessels having a side branch aperture. As described in that patent, the stent is manufactured with fixed length regions proximal and distal to the aperture. Thus, the stent may not be suitable in some patients because the fixed length of the proximal or distal region may interfere with collateral vessels upstream or downstream of the bifurcation. Accordingly, it would be desirable to provide a vascular prosthesis that includes a side branch aperture, but which has proximal and distal regions that may be tailored for a specific patient.

U.S. Pat. No. 5,824,037 to Fogarty et al. describes a modular intralumenal prosthesis, such as for a stent-graft, that includes a plurality of modules having standard interface ends for engaging adjacent modules. The modules employed in the prosthesis may include variations in axial length, cross-section, perimeter, resilient expansive force and axial flexibility. The modules are "locked" together by stitching a liner material.

One drawback of the prosthesis described in the Fogarty et al. patent is that the prosthesis may lack structural rigidity in the expanded configuration. In particular, the patent describes no mechanism to positively engage the modules other than the liner material. It therefore would be desirable to provide a modular stent wherein the modules cannot be locked together without stitching or a liner material.

The foregoing patent also does not teach that a modular stent may be used to improve conformance of the stent to a patient's vasculature when used in a bifurcated region, or the desirability of intermixing segments including different materials, including bioabsorbable or drug-eluting segments.

Therefore, it would be desirable to provide a vascular prosthesis including a plurality of modular segments interconnected by lockable joints that enhance articulation between adjacent segments during delivery of the prosthesis and enhance structural rigidity of the prosthesis in the deployed configuration.

It also would be desirable to provide a vascular prosthesis that includes a plurality of modular segments interconnected by a plurality of joints, in which the modular segments include different materials or strut configurations, thereby permitting the structural rigidity of the vascular prosthesis in the deployed configuration to be tailored for a specific patient or application.

It further would be desirable to provide a vascular prosthesis including a plurality of modular segments, wherein one or more segments may be bioabsorbable or drug-eluting, to provide predetermined doses of drug to the vessel wall or intravascularly to a desired tissue region.

Still further, it would be desirable to provide a vascular prosthesis that includes a plurality of modular segments, wherein one or more segments of customizable length may be intermixed to provide a desired feature, for example for the treatment of bifurcated vessels or aneurysms.

Still further, it would be desirable to provide a method for assembling a device wherein a physician could intermix device components formed of one or more interlocking modular segments, in order to provide a vascular prosthesis with radial force and structural rigidity tailored to a specific patient or application.

Still further, it would be desirable to provide a method for assembling a device wherein a physician could intermix device components that include one or more interlocking modular segments to make a customizable vascular prosthesis by snapping the components together without the need for assembly tools.

Still further, it would be desirable to provide a system for assembling a device that includes interlocking modular segments and interlocking modular end segments that can be joined to form a device having a customizable length, configuration or structural rigidity.

It also would be desirable to provide device components that include modular segments configured to be welded together, so to eliminate the need for traditional laser cutting of long tubular members.

SUMMARY OF THE INVENTION

In view of the foregoing, it is an object of the present invention to provide a vascular prosthesis that includes a plurality of modular segments interconnected by a plurality of inter-engageable elements forming joints, which enhance articulation between adjacent segments during delivery of the prosthesis and enhance structural rigidity of the prosthesis in the deployed configuration.

It is also an object of this invention to provide a vascular prosthesis that includes a plurality of modular segments interconnected by joints, wherein the modular segments are made with different materials or strut configurations and permit permitting the structural rigidity of the vascular prosthesis in the deployed configuration to be tailored for a specific patient or application.

It is another object of the present invention to provide a vascular prosthesis that includes a plurality of modular segments, one or more segments of which may be bioabsorbable or drug-eluting and provide predetermined doses of drug to the vessel wall or intravascularly to a desired tissue region.

It is a further object of the present invention to provide a vascular prosthesis that includes a plurality of modular segments, one or more segments of which may be intermixed to provide a desired feature and to have proximal and distal regions of customizable length, for example for the treatment of bifurcated vessels or aneurysms.

Still further, it is an object of the present invention to provide a method for assembling a device, by which a physician can intermix device components that include one or more interlocking modular segments, so to provide a vascular prosthesis with structural rigidity tailored to a specific patient or application.

Still further, it is an object of the present invention to provide a method for assembling a device, by which a physician can intermix device components that include one or more interlocking modular segments, so to provide a vascular prosthesis with variable radial force and/or variable structural rigidity, for example, for the treatment of plaque in blood vessels.

Still further, it is an object of the present invention to provide a system for assembling a device, by which interlocking modular segments and interlocking modular end segments can be joined to form a prosthesis of customizable length, configuration or structural rigidity.

Still further, it is an object of the present invention to provide a method for assembling a device which eliminates the need for laser cutting and processing different length devices by providing interlocking modular segments that a physician can intermix to form a customizable length device.

Still further, it is an object of the present invention to provide a method for assembling a device wherein a physician can intermix device components that include one or more interlocking modular segments to make a customizable vascular prosthesis by snapping the components together without the need for assembly tools.

Still further, it is an object of the present invention to provide modular segments configured to be welded together to eliminate the need for traditional laser cutting and expansion techniques of longer tubes, which have a disproportionately high scrap rate for longer stents and smaller stents.

These and other objects of the present invention are accomplished by providing a vascular prosthesis having a delivery configuration and an expanded configuration. The prosthesis includes a plurality of modular segments interengaged by flexible, and preferably lockable, inter-engageable elements that form joints. In accordance with the principles of the present invention, the segments may have a number of different characteristics and may be assembled by the clinician to customize the prosthesis for a specific patient or application.

For example, segments may have differing mechanical properties and may be self-expanding or balloon-expandable, and may include differing strut configurations and/or different materials, such as metal alloys or bioabsorbable or drug-eluting polymers. In addition, individual segments of the vascular prosthesis may include specific features, such as a side-branch aperture for bifurcated vessels or a covering for excluding an aneurysm.

In one embodiment, the inter-engageable element used to join the modular segments include ball and socket joints that facilitate articulation between adjacent segments during delivery of the stent through tortuous anatomy. Each segment includes proximal and distal ends, wherein each end includes a plurality of ball elements, socket elements or a combination of ball and socket elements, depending upon the mechanical properties, strut configuration and intended purpose of a given segment. For example, where a segment includes a hoop having a plurality of generally zig-zag struts, the ball and socket elements may be formed on extensions of the struts of adjacent segments.

In an alternative embodiment, the inter-engageable elements used to join the interlocking modular segments include a substantially ring shaped male interface element and a rounded female interface element. Each segment includes struts and bends. Each segment also has a proximal end and a distal end, wherein each end includes a plurality of ring shaped male interface elements, rounded female interface elements, or a combination of male and female interface elements, depending upon the mechanical properties, strut configuration and intended purpose of a given segment. The ring shaped male interface element and rounded female interface element can be joined and locked so the interlocking modular segments are joined to form a prosthesis having a customizable length, configuration or structural rigidity.

In another alternative embodiment, the modular segments include welding zones in the connector areas. The modular segments of this embodiment include a zig-zag configuration of struts and bends. The welding zones include a rounded protrusion formed at the end of one or more selected bends on one side of a segment and tongs at the end of one or more selected bends on the opposite side of the segment. The rounded protrusions of one segment join and inter-engage with the tongs on an adjoining segment at the connector areas of the device components.

In still another alternative embodiment, the inter-engageable elements used to join the modular segments include intertwined spiral elements that facilitate articulation between adjacent segments during delivery of the stent through tortuous anatomy. Each segment includes proximal and distal ends, wherein each end includes a spiral element that interengages a spiral element of an adjacent segment. The spiral elements have a common orientation, either clockwise or counterclockwise, depending upon the mechanical properties, strut configuration and intended purpose of a given segment. Each segment illustratively may include a hoop having a plurality of generally zig-zag struts, wherein the spiral elements extend may be formed on extensions of the struts of at regular intervals.

In accordance with a preferred aspect of the present invention, interconnected joints are configured to lock when the prosthesis is transitioned from the delivery configuration to the deployed configuration. For example, the socket elements may include a pliers-like element that closes to grip the ball elements when the segment is deployed, thereby preventing adjacent segments from disengaging in the deployed configuration. In the alternative embodiment, the interference of the interconnected spiral elements may increase, thereby locking the spiral elements together.

In alternative embodiments of the prosthesis of the present invention, axial flexibility of the prosthesis may be further enhanced by incorporating flexible, physical connections between the struts contained within a given segment.

Delivery systems for delivering the inventive prostheses of the present invention also are provided.

BRIEF DESCRIPTION OF THE DRAWINGS

The foregoing and other objects of the invention will be apparent upon consideration of the following detailed description, taken in conjunction with the accompanying drawings, in which like reference characters refer to like parts throughout, and in which:

FIG. 11 is a plan view of an embodiment of a modular vascular prosthesis of the present invention that has been cut along line A-A and flattened in which the interconnected joints include intertwined spiral elements;

FIGS. 12A and 12B are, respectively, perspective views of the modular vascular prosthesis of FIG. 1 disposed in the delivery configuration around a balloon catheter and in the deployed configuration;

DETAILED DESCRIPTION OF THE INVENTION

Figure 1:
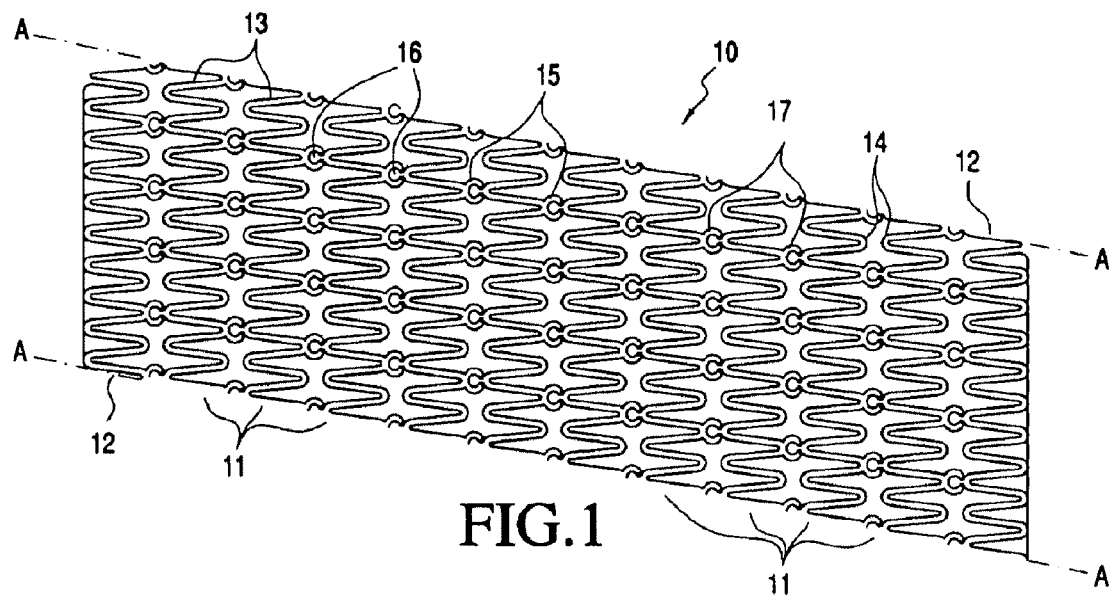
FIG. 1 is a plan view of an exemplary modular vascular prosthesis constructed in accordance with the principles of the present invention that has been cut along line A-A and flattened.

Referring to FIG. 1, a first family of embodiments of a vascular prosthesis of the present invention is described. Vascular prosthesis 10, for example, a stent, is shown cut along line A-A along its longitudinal axis and flattened into a plane for illustrative purposes. Vascular prosthesis 10 includes a tube-like structure made up of a plurality of interconnected modular segments, including inner segments 11 and end segments 12. In the illustrated embodiment, segments 11 and 12 include a plurality of struts 13 joined at the ends by bends 14 to form a generally zig-zag configuration in the deployed configuration. As would be understood by one of ordinary skill in the art, segments 11 and 12 may include many alternative strut configurations without departing from the scope of the present invention.

In accordance with the principles of the present invention, joints 15 interconnect segments 11 and 12. In a first preferred embodiment, each joint 15 includes ball element 16 engaged within socket element 17. Inner segments 11 include ball elements 16 and socket elements 17 at either end, while end segments 12 include such elements on only one end. Ball elements 16 and socket elements 17 preferably are formed as extensions on selected bends 14 disposed between struts 13 around the circumference of the stent.

In FIG. 1, ball elements 16 are disposed on one end of each inner segment 11 while socket elements 17 are disposed on the other end of the segment. Adjacent ball or socket elements are depicted as having one intervening bend 14 around the circumference of the stent, but may include two or more intervening bends. Joints 15 permit a significant degree of articulation between adjacent segments, particularly in the delivery configuration, making the stent highly flexible and thus able to negotiate tortuous anatomy. Although ball elements illustratively are shown as substantially circular structures, ball elements 16 and the corresponding sockets may have other suitable shapes, such as ovals, polygons or diamonds.

The zig-zag configuration of struts 13 and bends 14 depicted in FIG. 1 preferably is formed by laser cutting a solid tube. Vascular prosthesis 10 preferably is flexible enough to conform to the shape of a delicate vessel without substantially remodeling the vessel. In particular, the zig-zag configuration of segments 11 and 12 is expected to conform to a natural curvature of a vessel wall. Of course, other patterns of struts and bends, such as are known in the art, advantageously be used within segments 11 and 12.

Figure 2A:
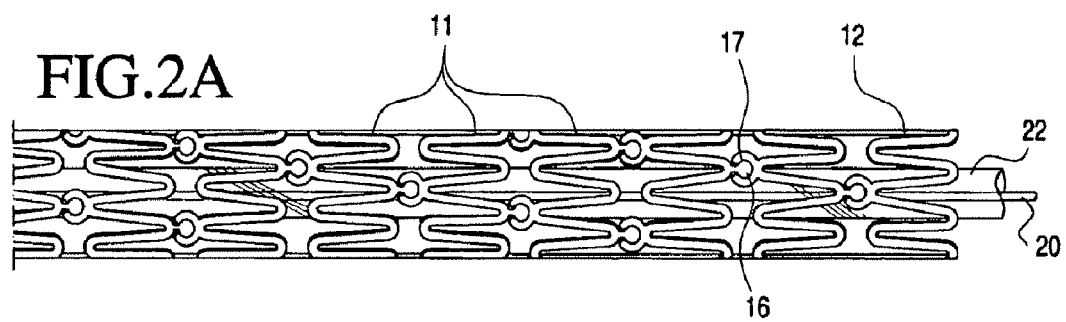
FIGS. 2A and 2B are, respectively, perspective views of the modular vascular prosthesis of FIG. 1 disposed in the delivery configuration around a balloon catheter and in the deployed configuration.

Referring to FIG. 2A, vascular prosthesis 10 includes a balloon expandable material and is shown crimped in a contracted delivery configuration over balloon 20 of balloon catheter 22. This may be accomplished by assembling a desired number of inner segments 11 between end segments 12 to provide a stent of a desired length, and the assembled stent may then be crimped onto balloon 20 using any of a number of previously-known crimping devices. Because the stent is retained centered on balloon 20, ball elements 16 and socket elements 17 remain in engagement to form a substantially smooth exterior surface of the stent.

Balloon catheter 22 is delivered transluminally to a target site within a patient's vessel using, for example, well-known percutaneous techniques. Vascular prosthesis 10 or portions of catheter 22 may be radiopaque to facilitate positioning within the vessel. The target site may, for example, include a stenosed region of the vessel at which an angioplasty procedure has been conducted. In accordance with the present invention, joints 15 permit vascular prosthesis 10 to flex along its length to negotiate tortuous anatomy.

Figure 2B:
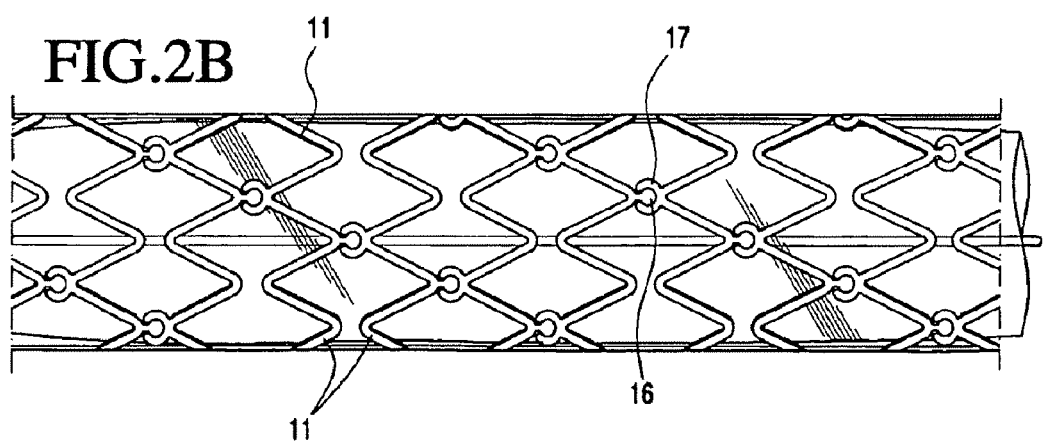

Referring to FIG. 2B, balloon 20 is inflated to expand vascular prosthesis 10 to the deployed configuration in which it engages and supports the wall of the vessel at the target site. As shown in FIG. 2B, ball elements 16 continue to be retained in the socket elements 17 when segments 11 and 12 are radially expanded. Balloon 20 is then deflated and balloon catheter 22 is removed from the vessel, leaving vascular prosthesis 10 supporting the vessel. The web structure of vascular prosthesis 10 provides sufficient radial stiffness to maintain vascular prosthesis 10 in the expanded configuration, with minimal recoil. Vascular prosthesis 10 optionally may include an external coating configured to inhibit restenosis.

Figure 3:
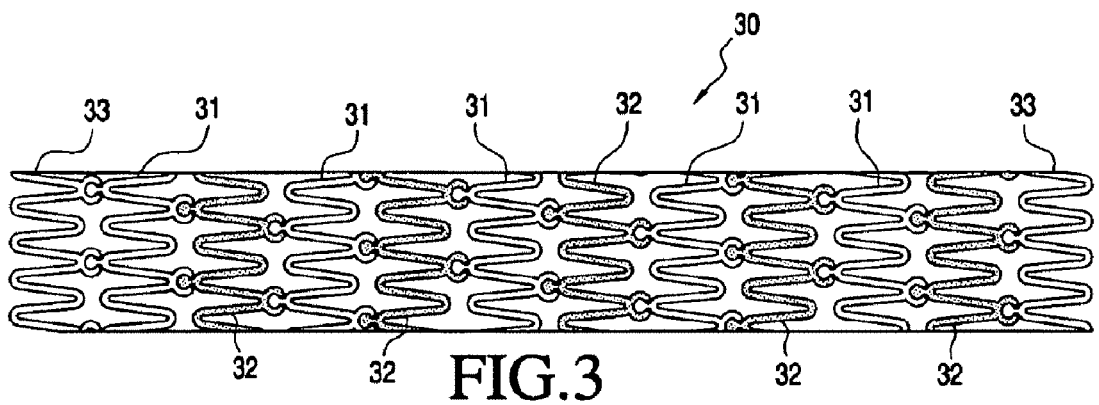
FIG. 3 is a side view of the vascular prosthesis of FIG. 1 wherein alternating segments include different materials.

Referring to FIG. 3, in accordance with one aspect of the present invention, inner segments 11 may include different materials, strut configurations, or types of radially expandable segments that are selectively intermixed to customize the vascular prosthesis for a specific patient or application. Segments also may include side-branch apertures for use in treating bifurcated vessels, graft covered segments for excluding aneurysms and drug-eluting segments that are pre-loaded with a predetermined amount of drug and may be assembled to provide a desired dose.

For example, whereas metallic radially expandable inner segments provide increased radial stiffness in the deployed configuration, bioabsorbable or drug-eluting radially expandable segments may be better suited for drug delivery. In the embodiment of FIG. 3, vascular prosthesis 30 includes five metallic segments 31 alternating with five drug-eluting segments 32, all disposed between end segments 33. In a preferred embodiment, the drug may include a tetrazole-containing rapamycin for use in treating restenosis, such as described in U.S. Pat. No. 6,015,815 to Mollison, which is incorporated herein by reference in its entirety.

Alternatively, because joints 34 include ball elements 35 and socket elements 36 that are common for segments 31, 32 and 33, the segments may be assembled in any order desired for a specific patient or application. Thus, for example, segments 32 and 33 may be reordered so that the five metallic segments are at one end of the stent, and the five polymeric segments are at the other end. Of course, as would be appreciated by those of skill in the art, many other combinations of materials are possible without departing from the scope of the invention.

Figure 4:
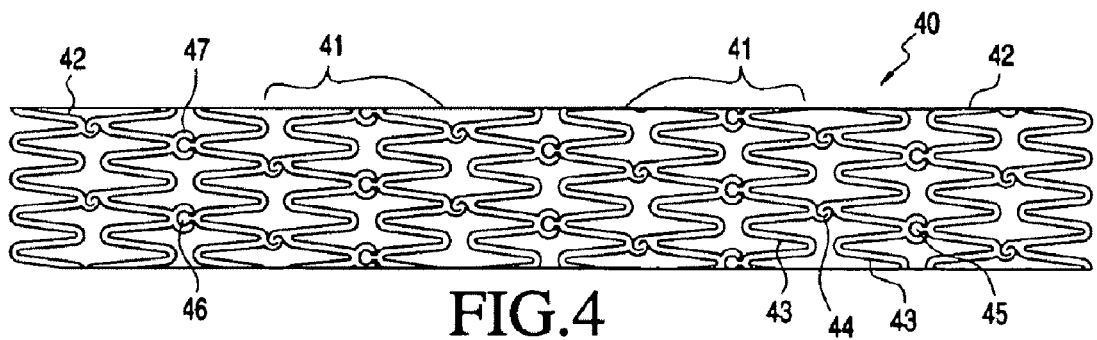
FIG. 4 is a side view of the vascular prosthesis of FIG. 1 wherein each segment includes additional flexible interconnections.

Referring to FIG. 4, in accordance with a further embodiment of the present invention, vascular prosthesis 40 includes a plurality of inner segments 41 disposed between end segments 42. Each inner segment 41 illustratively includes two zig-zag hoops 43 coupled by spiral joints 44 to further increase the longitudinal flexibility of the segment. Segments 41 further include joints 45 including ball elements 46 and socket elements 47 that enable the segment to be coupled to adjacent segments 41 and end segments 42 to assemble the stent to a desired length. As for the previous embodiments, joints 45 also enhance flexibility of the stent during transluminal insertion.

Figure 5:
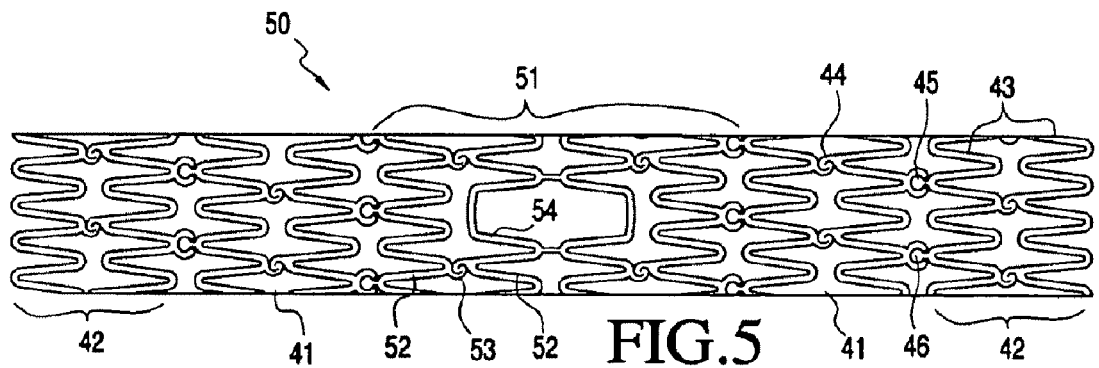
FIG. 5 is a side view of a prosthesis constructed in accordance with the present invention wherein one segment includes a portion defining a side-branch aperture.

Referring to FIG. 5, an alternative embodiment of vascular prosthesis 40 suitable for use in a bifurcated vessel is described. As noted hereinabove, stents having side-branch openings are known in the art, such as described in the aforementioned Von Oepen patent. One of the difficulties of such previously-known stents is that the regions proximal and distal to the side-branch opening are fixed at the time of manufacture and may be unsuitable for a particular patient. For example, the proximal or distal region may partially occlude collateral vessels.

Stent 50 of FIG. 5 solves this foregoing problem by permitting the clinician to tailor the lengths of the proximal and distal regions as desired for a specific patient or application. In particular, stent 50 includes inner segments 41 and end segments 42 as depicted in FIG. 4, where each segment 41 and 42 further includes hoops 43 coupled by spiral joints 44 and ball and socket elements 45 and 46, respectively. In addition, stent 50 includes inner segment 51 including hoops 52 coupled by spiral joints 53 and defining side-branch aperture 54.

Illustratively, stent 50 includes single segment 41 coupled on either side, however, it is to be understood that any number of segments 41 could be coupled on either side of inner segment 51. In addition, more than one inner segment 51 may be employed, with the side-branch apertures 54 disposed at different circumferential orientations, thereby enabling access to multiple side branch vessels. Accordingly, the vascular prosthesis of the present invention may be assembled by the clinician to match the anatomy of a specific patient's vasculature shortly before implantation and inner segments of various lengths and configurations may be intermixed as necessary to match the patient's vasculature.

Figure 6:
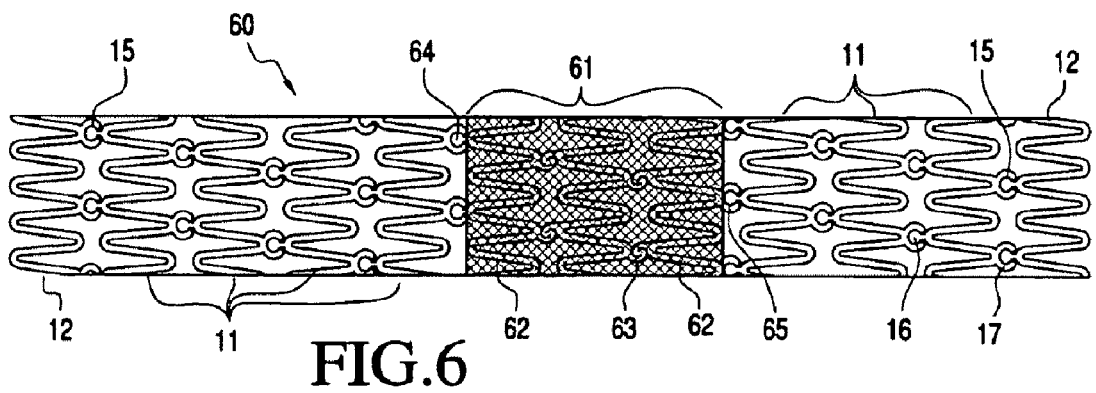
FIG. 6 is a side view of a prosthesis constructed in accordance with the present invention wherein one segment includes a graft covering for use in excluding an aneurysm.

With respect to FIG. 6, a further alternative embodiment of the vascular prosthesis of the present invention is described for use in excluding an aneurysm. Stent 60 is similar in design to the stent of FIG. 1, except that it includes a graft covered segment. More particularly, stent 60 includes a plurality of inner segments 11 interposed between end segments 12. Each of inner segments 11 includes ball and socket elements 16 and 17, respectively, that engage a corresponding element on an adjacent segment to form joints 15.

Stent 60 further includes inner segment 61, illustratively having a configuration similar to that of segment 41 of FIG. 4. In particular, segment 61 includes zig-zag hoops 62 coupled by spiral joints 63, with the outermost hoops including ball elements 64 and socket elements 65 that engage the adjacent segments. In accordance with this aspect of the present invention, segment 61 includes graft covering, such as Dacron or expanded polytetrafluoroethylene (ePTFE), affixed to its outer surface by a biocompatible adhesive or sutures. In this manner, stent 60 may be assembled to include one or more segments 61 to exclude an aneurysm within a vessel, yet continue to permit blood flow to reach healthy vessel wall upstream and downstream of the aneurysm.

Figure 7:
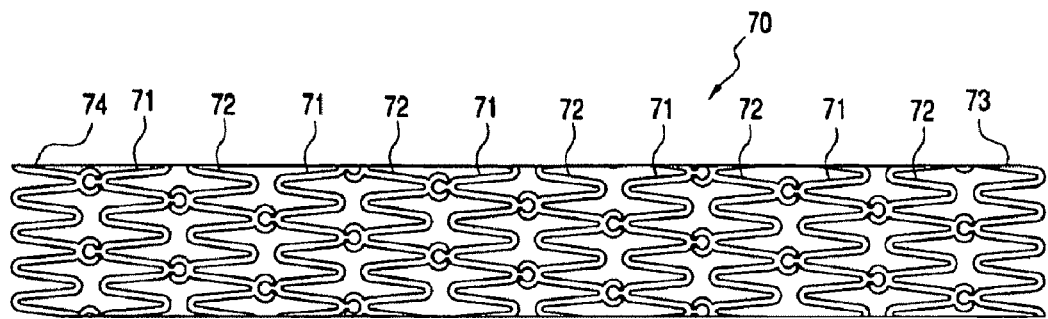
FIG. 7 is a side view of an alternative embodiment of the prosthesis of the present invention wherein alternating modular segments include either all ball elements or all socket elements.

Referring to FIG. 7, a further alternative embodiment of the vascular prosthesis of the present invention is described. Vascular prosthesis 70 includes inner segments 71, inner segments 72 and end segments 73 and 74. Each segment 71-74 includes a plurality of struts joined by bends to form zig-zag hoops. Whereas inner segments 11 of the embodiment of FIG. 1 included ball elements at one end and socket elements at the other, segments 71 include only ball elements at either end and segments 72 include only socket elements at either end. End segment 73 includes only ball elements at one end and end segment 74 includes only socket elements at one end. As will be understood, segments 71 and 72 may include the same or different strut configurations, may be of the same or different lengths or may have the same or different mechanical properties.

Figure 8:
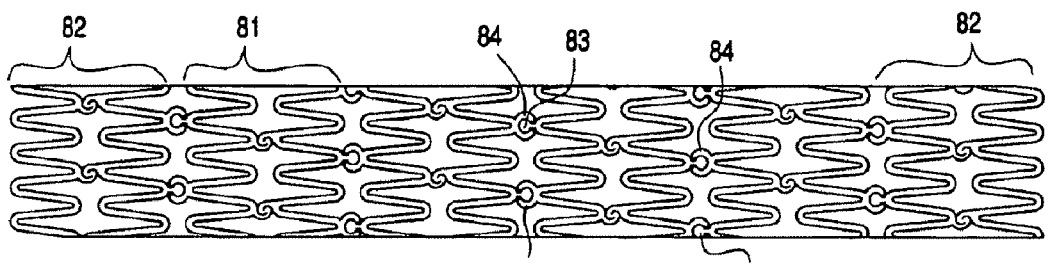
FIG. 8 is a side view of an alternative embodiment of the prosthesis of the present invention wherein each segment that combines both ball and socket elements at each end.

Referring now to FIG. 8, a still further alternative embodiment of the vascular prosthesis of the present invention is described. Vascular prosthesis 80 is similar in construction to stent 40 of FIG. 4, and includes inner segments 81 and end segments 82. Unlike inner segments 41, which included only ball elements at one end and socket elements at the other, segments 81 have ball elements 83 alternating with socket elements 84 around the circumference of the segment at either end.

As for the previous embodiments, segments 81 may have the same or different strut configuration, the same or different lengths or the same or different mechanical properties.

Figure 9A:
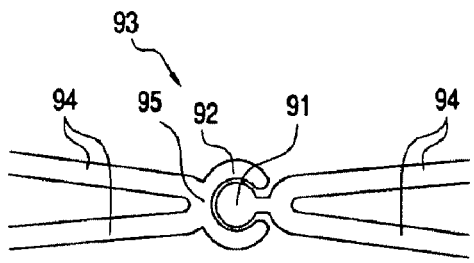
FIGS. 9A and 9B are, respectively, side views of a locking ball and socket joint of the present invention depicted in the delivery configuration and the deployed configuration.
Figure 9B:
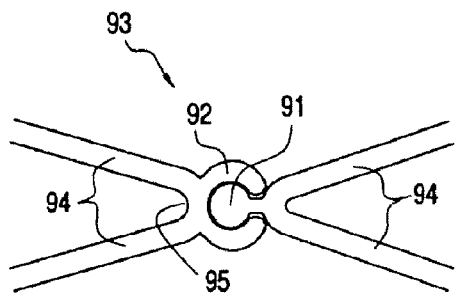

With respect to FIGS. 9A and 9B, in accordance with a further aspect of the invention, locking joints suitable for use in the vascular prostheses of FIGS. 1-8 are described. Ball elements 91 and socket elements 92 of FIG. 9 are designed to add structural rigidity to joints 93 of a vascular prosthesis in the deployed configuration. In particular, as zig-zag segments 94 expand from the delivery configuration (FIG. 9A) to the expanded deployed configuration (FIG. 9B), socket element 92 functions as pliers that partially closes around ball element 91, thereby fixedly engaging the ball element and enhancing the structural rigidity of the assembled prosthesis.

To facilitate this pliers-like action of socket elements 92, bends 95 preferably include reduced thickness regions, thereby facilitating expansion of the segments into the deployed configuration. Providing thinner bends 95 also promotes closing of socket element 92 around ball element 91 as the arms of the socket element are forced together during expansion of the vascular prosthesis, as depicted in FIG. 9B. Advantageously, the closing action of socket element 92 about ball element 91 reduced the risk of disengagement of adjacent segments of vascular prosthesis in the deployed configuration.

Figure 10:
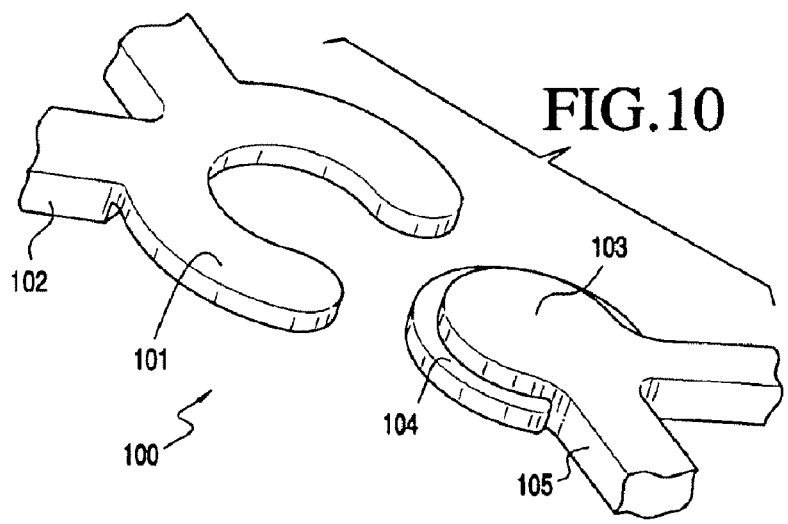
FIG. 10 is a perspective view of further alternative ball and socket joint that permits self-expanding segments and balloon-expandable segments to be intermixed.

With respect to FIG. 10, a further embodiment of a ball and socket joint suitable for use with vascular prosthesis of the present invention is described. In the preceding embodiments the socket elements generally are of uniform thickness. In FIG. 10, however, joint 100 includes socket element 101 has a thickness equal to about have of strut thickness 102 and ball element 103 including flange 104, wherein the flange also has a thickness of about one-half strut thickness 105. When coupled together, ball element 103 projects into socket element 101, while flange 104 bears against the underside of socket element 101. In this manner, ball element 103 is free to articulate within socket element 101, but flange 104 prevents ball element 103 from passing entirely through the socket element.

Joint embodiment of FIG. 10 may be particularly advantageous when used in conjunction with the stent of FIG. 7, especially where the inner segments 71 and 72 are selected to have different radial expansion properties, e.g., such as resilient self-expanding segments and rigid balloon-expandable segments. If segments 72 (which have all socket elements) are made of a rigid balloon-expandable material and segments 71 (which have all ball elements) are made of a resilient self-expanding material, joints 100 may be used to facilitate crimping the assembled stent onto a balloon catheter. In particular, because ball elements 103 are captured by flange 104 within socket 101, the self-expanding segments will be compressed onto the balloon when the rigid segments are crimped onto the balloon.

In addition, because joints 101 may be configured to provide the locking feature described with respect to the embodiment of FIG. 9, joints 100 also may be used to lock the segments of the stent together in the deployed configuration, thereby preventing disengagement of adjacent segments.

Figure 18:
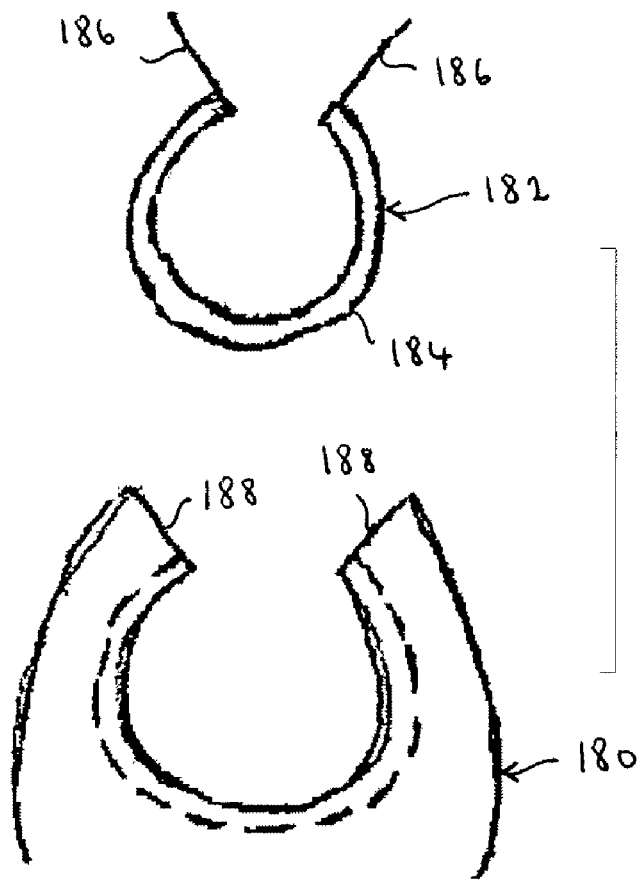
FIG. 18 is a plan view of an alternative ring-shaped male interface element and a rounded female interface element that permits joining and intermixing of interlocking modular segments.

An alternative embodiment of the invention is shown in FIG. 18. This embodiment provides a method for assembling self-expanding medical devices that can be customized in various ways. This alternative inter-engagement method uses interlocking modular segments that include a rounded female interface element 180, which has edges 188, and a substantially ring-shaped male interface element 182, which has a ring 184 and two tails 186 extending off the ends of the ring at angles. These two interface elements 180 and 182 can be coupled together, so that male interface element 182 projects into female interface element 180 and ring 184 inter-engages in a snap fit against the underside of female interface element 180. In this way, the male and female interface element are held together by radial force. In this snap fit configuration, tails 186 of male interface element 182 bear against edges 188 of female interface element 180. As it can be seen from FIG. 18, the ring-shaped construction of male interface element 182 provides for a lighter, more mesh-like stent than constructions, in which the male interface element is a solid disk. Further, the ring-like shape of male interface element 182 makes it more adaptable to engage with female interface element 180, in the event that the two profiles did nor exactly coincide, and also more adaptable to a shape change during expansion of the vascular prosthesis.

Figure 19:
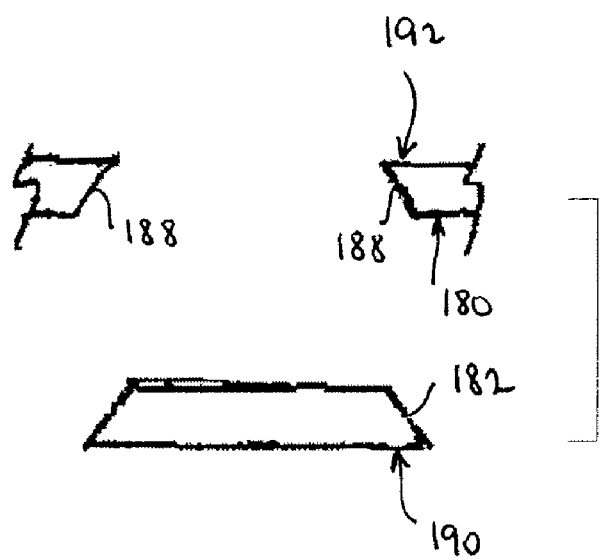
FIG. 19 is a side view of an interlocking modular segment as seen from both the proximal and distal ends of an interlocking modular segment.

FIG. 19 shows partial side views of the inter-engagement mechanism as seen from both the proximal and distal ends of an interlocking modular segment of this embodiment. As will be discussed in more detail herein, the circular interlocking feature ensures that the interlocking modular segments of this embodiment do not move axially in relation to each other and will not separate in a radial direction. FIG. 19 further shows that rounded female interface element 180, which is part of a first segment 190, and ring-shaped male interface element 182, which is part of a second segment 192, have matching beveled edges, which promote the relative positioning and interlocking of the male and female interface elements 180 and 182 by sliding one onto the other, in contrast, for example, with configurations in which step-shaped edges are present.

The interlocking construction depicted in FIGS. 18 and 19 not only enables a clinician to assemble a prosthesis of a desired length from a plurality of segments of shorter lengths, but also enables the clinician to tailor stent properties as desired along the axial length of the prosthesis. For example, a clinician may desire to implant a prosthesis having certain segments with higher or lower mechanical properties than others, in terms of tensile and compressive strength but also radial expansion strength, longitudinal flexibility, torsional resistance and/or resistance to foreshortening. It may also be desired to have certain segments of the prosthesis expand at different rates or to different degrees than others, in order to provide a prosthesis having segments of different diameters after expansion, or having a generally frustoconical shape, or having a first segment expand faster than a second segment, so that the locking interfaces in second segment move towards and engage the locking interfaces in the first segment. Further, a clinician may desire to employ a prosthesis having different strut arrangements along its length, so that a prosthesis may be assembled having a first strut arrangements in the first segment, a second strut arrangement in the second segments, and so on.

Moreover, a prosthesis constructed according to the principles of the present invention may include pairs of segments that are interlocked in a substantially homogeneous manner around their circumference, and other pairs of segments that are interlocked only along a portion of the circumference, and/or other pairs of segments that have more male-female interlocking connections along a portion of the circumference than along the remainder of the circumference. The last two constructions are particularly suited for applications where the prosthesis must be positioned at a Y-shaped, bifurcated vessel junction, more particularly, along to the leg of the "Y" and also along one of the branches of the "Y". In this situation, the clinician arranges the prosthesis such that the portion of the circumference with fewer or no interlocking points is disposed at the "Y" junction, producing a prosthesis that is has one or more openings at the "Y" junction. For example, the prosthesis may be positioned such to have larger cells at the "Y" junction, or to have an opening at the "Y" junction, or to develop an opening by further expanding a balloon at the "Y" junction and by causing some of the interlocking connections to open up.

Figure 20:
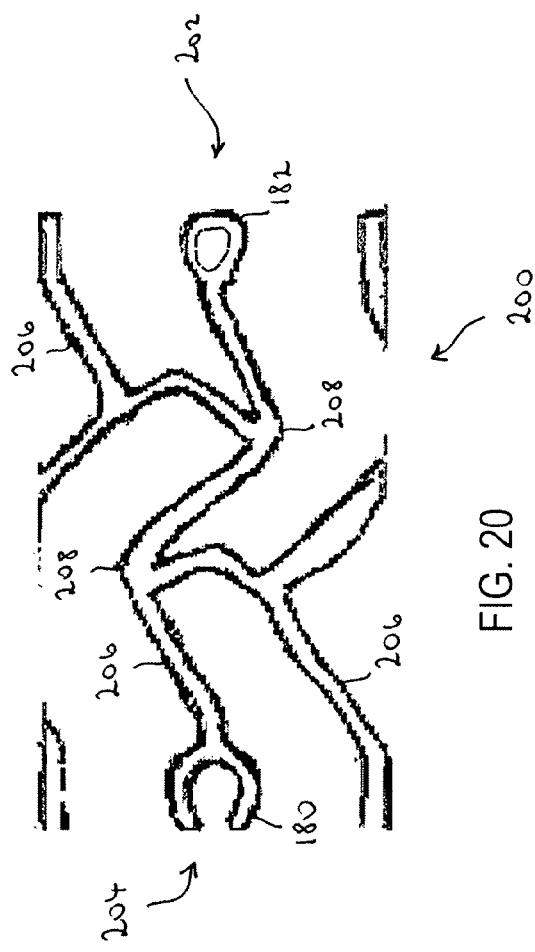
FIG. 20 is a detail view of an interlocking modular segment in an embodiment of the invention.

FIG. 20 illustrates an interlocking modular segment 200 of the present embodiment. Segment 200 has a proximal end 202 and a distal end 204 and includes a plurality of struts 206 and bends 208 in an angled branch configuration. The network of struts 206 and bends 208 form angles where the struts change direction and branches where struts branch off from each other. As would be understood by one of ordinary skill in the art, interlocking modular segment 200 may include alternative strut configurations. Substantially ring-shaped male interface elements 182 and rounded female interface elements 180 are formed as extensions on selected struts at the ends of segment 200. In some embodiments, the substantially ring-shaped male interface element 182 is disposed at the proximal end of the interlocking modular segment, and the rounded female interface element 180 is disposed at the distal end of segment 200.

Figure 21:
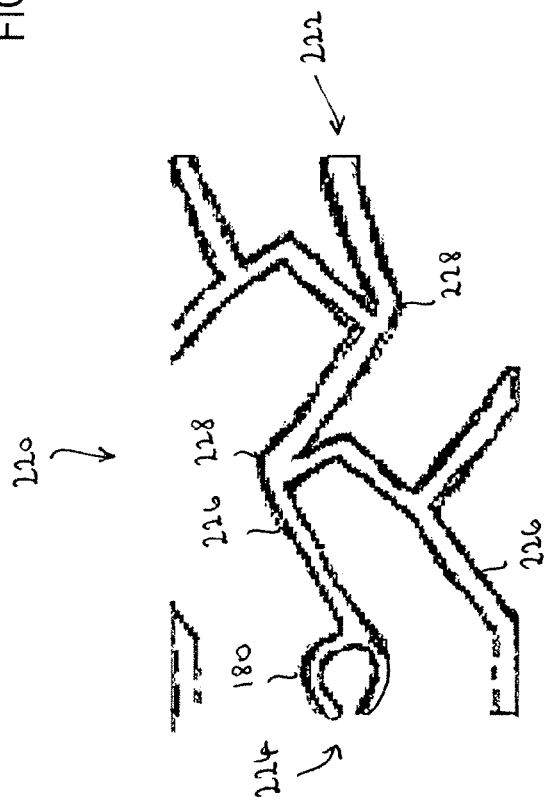
FIG. 21 is a detail view of the first end of an interlocking modular segment in an embodiment of FIG. 20.

FIG. 21 shows an interlocking first end modular segment in accordance with this embodiment. The first end segment 220 has a proximal end 222 and a distal end 224 and includes a plurality of struts 226 and bends 228. At its distal end 224, the first end segment includes a rounded female interface element 180. It should be noted that the first end segment has no interface element at its proximal end 222 because as an end segment, it forms the end of an assembled medical device and does not require inter-engagement with other modular segments at its proximal end.

Figure 22:
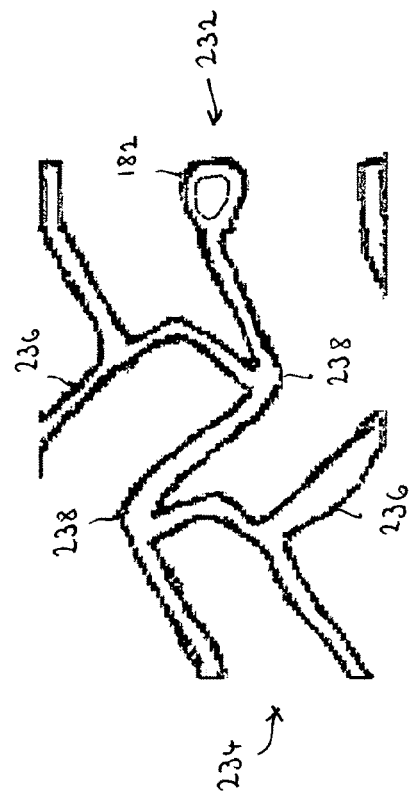
FIG. 22 is a plan view of the second end of an interlocking modular segment in an embodiment of FIG. 20.

FIG. 22 shows an interlocking second end modular segment in accordance with this embodiment. The second end segment 230 has a proximal end 232 and a distal end 234 and includes a plurality of struts 236 and bends 238. The second end segment includes a substantially ring-shaped male interface element 182 at its proximal end 232. There is no interface element at the distal end of the second end segment. This is because it is an end segment that forms the end of an assembled medical device and does not require inter-engagement with other modular segments at its distal end.

Alternatively, an interlocking modular segment may have a substantially ring-shaped interface element at each of the proximal and distal ends of the segment or a rounded female interface element at each of the proximal and distal ends. In other words, an interlocking modular segment may have two male interface elements or two female interface elements instead of one of each. In such cases, the double male and double female segments would be joined to each other as the medical device is assembled and alternate along the length of the device.

Figure 23:
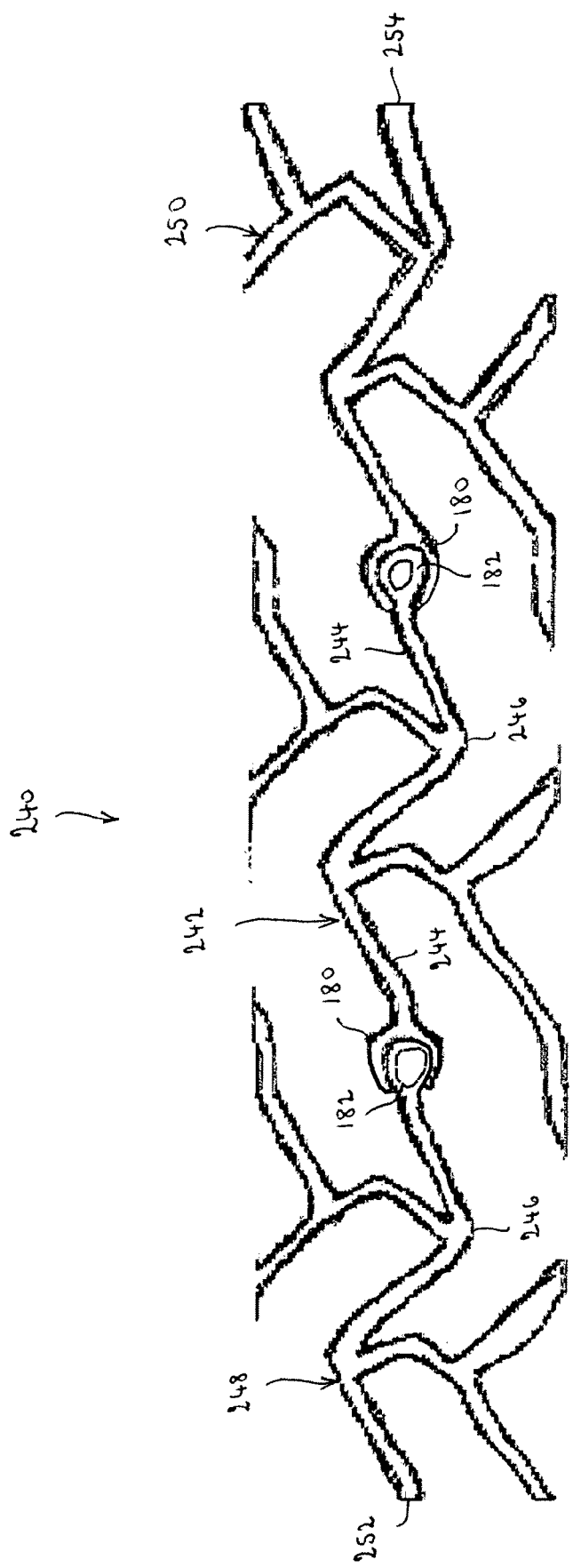
FIG. 23 is a plan view of a section of a modular vascular prosthesis assembled using methods and systems of the present invention.

FIG. 23 illustrates an expanded view of a portion of a vascular prosthesis assembled with interlocking modular segments employing the substantially ring-shaped male interlocking element and the rounded female interlocking element of this embodiment. Vascular prosthesis section 240 includes a plurality of interconnected modular segments 242, which include a plurality of struts 244 and bends 246 that may be arranged in various patterns. In addition, FIG. 23 shows that these segments include interlocking modular segments 242, which provide the inner segments of the prosthesis, as well as interlocking first end modular segments 248, which provide the proximal end 252 of the prosthesis, and interlocking second modular end segments 250, which provide the distal end 254 of the prosthesis. In accordance with the principles of this embodiment, inner segments 242 are interconnected by the joining of interlocking mechanism of the ring-shaped male element 180 at the proximal end of segment 242 and the rounded female element 180 of segment 248. The device components can be provided to physicians in, e.g., 5 mm components or other lengths depending on the needs of the physician.

Toward proximal end 252 of the prosthesis, the proximal ends of the inner interlocking modular segments 242, interconnect with the distal ends of the first end modular segments 248. These interconnections are made by the substantially ring-shaped male element 182 of an inner segment 242 joining in inter-engagement with the rounded female element 180 of a first end segment 248. Similarly, toward the distal end 254 of the prosthesis, the distal ends of the inner interlocking modular segments 242, interconnect with the proximal ends of the second end modular segments 250 when the rounded female element 180 of an inner segment 242 inter-engages a substantially ring-shaped male element 182 of a second end segment 250. The circular interconnection mechanism ensures that the different interlocking modular segments do not move axially relative to one another. Moreover, this mechanism together with the super-elastic properties of the alloys used to make the interlocking modular segments ensures that the segments do not separate in a radial direction.

Figure 24A:
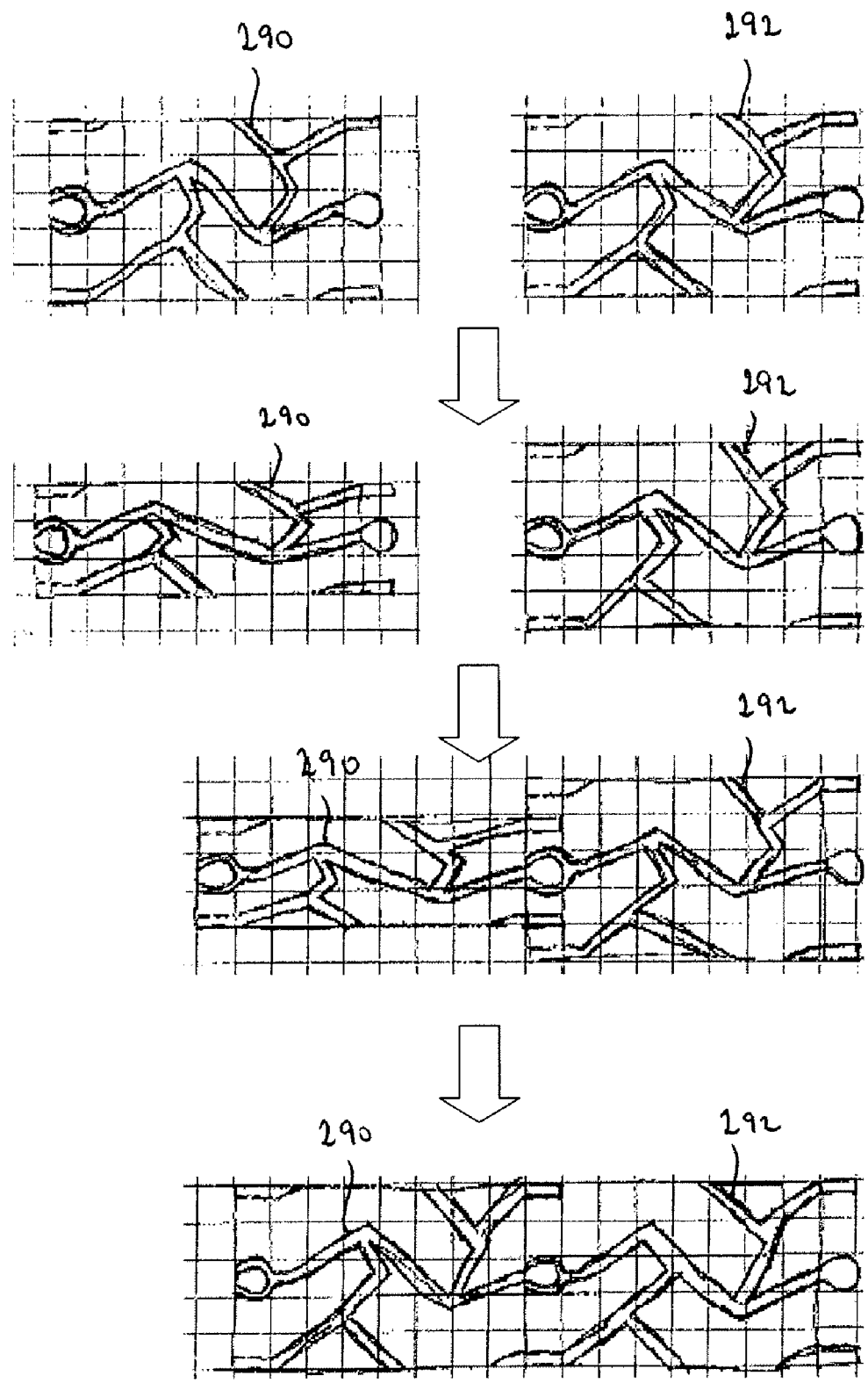
FIGS. 24A, 24B and 24C are, respectively, a figure sequence illustrating a method of assembling the modular vascular prosthesis of FIG. 23, and plan and perspective views of the modular vascular prosthesis of FIG. 23 disposed in the delivery configuration around a balloon catheter and in the deployed configuration.

Referring to FIG. 24A, a first segment 290 and a second segment 290 and 292 may be interlocked as follows. First segment 290 and second segment 292 may be provided as separate elements (first step). First segment 290 may then be collapsed, while second segment 292 may be left in its original condition (second step). First segment 290 may then be positioned axially in relation to second segment 292 (third step). First segment 290 may then be expanded again, for example, by removing a collapsing mechanism, interlocking first segment 290 with second segment 292.

Figure 24B:
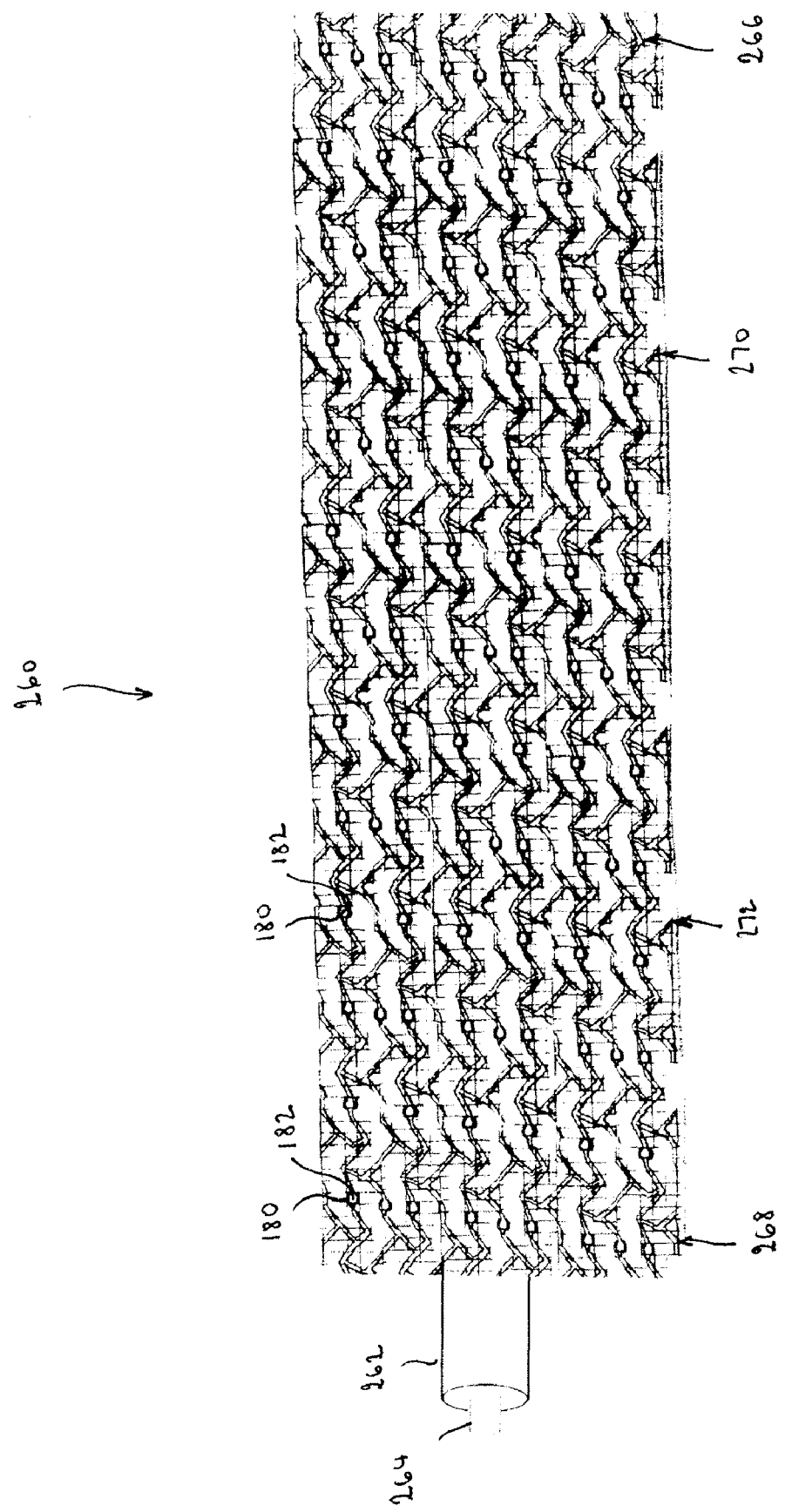

Referring now to FIG. 24B, a vascular prosthesis using the interlocking mechanism of this embodiment is shown. Vascular prosthesis 260 includes a balloon expandable material and is shown crimped in a contracted delivery configuration over balloon 262 of balloon catheter 264. This may be accomplished by assembling a desired number of inner segments 270, 272 between first end segments 266 and second end segments 268 to provide a stent of a desired length, and the assembled stent may then be crimped onto balloon 262 using any of a number of previously-known crimping devices. Because the stent is retained centered on balloon 262, the substantially ring-shaped male interlocking elements 182 and rounded female interlocking elements 180 remain in engagement to form a substantially smooth exterior surface of the stent.

Balloon catheter 262 is delivered transluminally to a target site within a patient's vessel using, for example, well-known percutaneous techniques. Vascular prosthesis 260 or portions of the catheter may be radiopaque to facilitate positioning within the vessel. The target site may, for example, include a stenosed region of the vessel at which an angioplasty procedure has been conducted. In accordance with the present invention, inter-engagement of substantially ring-shaped male interlocking elements 182 and rounded female interlocking elements 180 permit vascular prosthesis 260 to flex along its length to negotiate tortuous anatomy.

Alternatively, vascular prosthesis 260 may be self-expanding, that is, be manufactured from a shape memory material such as Nitinol (a nickel-titanium alloy) and be caused to self-expand at the target location in a vessel using techniques known in the art. Typically, vascular prosthesis 260 is disposed on a delivery catheter in a contracted state and the delivery catheter having the prosthesis disposed thereon is covered with a sheath. The delivery catheter is then inserted into a patient's body intra-vascularly, and when the target location is reached, the sheath is withdrawn allowing the prosthesis to self-expand.

When a self-expanding structure is employed, vascular prosthesis 260 may be delivered pre-assembled (for example, by interlocking male and female elements mechanically, or by bonding or welding), or may be allowed to assemble in situ by delivering vascular prosthesis 260 as a plurality of separate segments that become interlocked during the expansion process.

Alternatively, vascular prosthesis 260 may be balloon-expandable, and the different modular segments be delivered interlocked or may interlock during expansion in a predetermined sequence by inflating the catheter balloon and by causing the different segments to deploy at different speeds and/or times.

In one embodiment of the invention, vascular prosthesis 260 is formed by one or more segments that are balloon expandable, and one or more segments that are self-expanding. This configuration may be useful, for example, for disposing a stent within a Y-shaped vessel branch, as described in greater detail below.

Figure 24C:
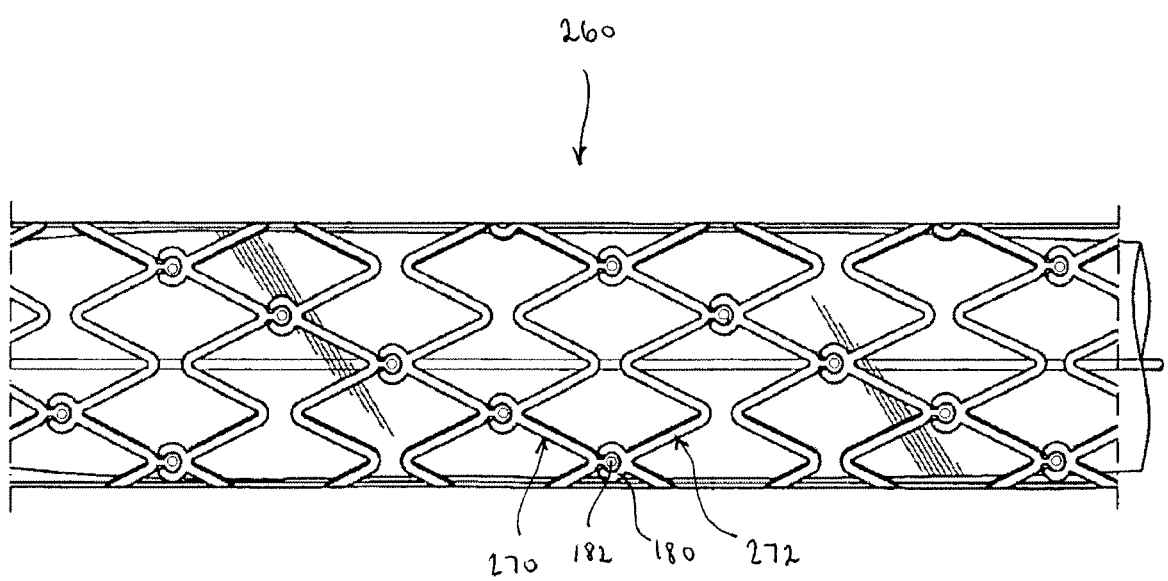

Referring to FIG. 24C, balloon 262 is inflated to expand vascular prosthesis 260 to the deployed configuration in which it engages and supports the wall of the vessel at the target site. As shown in FIG. 24C, the substantially ring-shaped male interlocking elements 182 continue to be retained in rounded female interlocking elements 180 when modular interlocking segments 270 and 272 are radially expanded. Balloon 262 is then deflated and balloon catheter 264 is removed from the vessel, leaving vascular prosthesis 260 supporting the vessel. The web structure of vascular prosthesis 260 provides sufficient radial stiffness to maintain vascular prosthesis 260 in the expanded configuration, with minimal recoil. Vascular prosthesis 260 optionally may include an external coating configured to inhibit restenosis.

Figure 25:
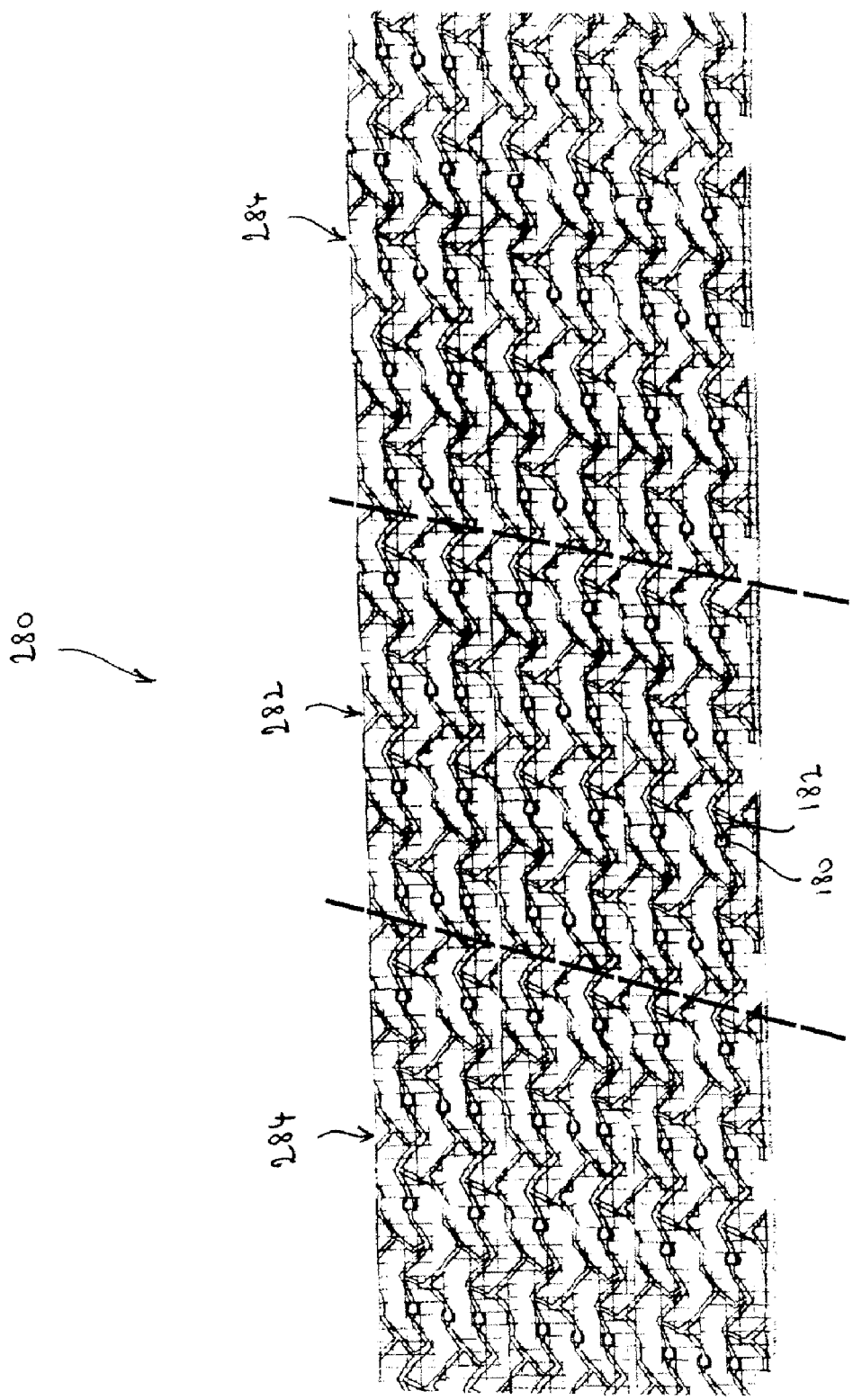
FIG. 25 is a perspective view of the vascular prosthesis of FIG. 23 wherein alternating groups of segments include material of relative radial strength and weakness.

Turning to FIG. 25, in accordance with one aspect of the present invention, the segments may include different materials, strut configurations, wall thicknesses, and/or different types of radially expandable segments that are selectively intermixed to customize the vascular prosthesis for a specific patient or application. For example, one segment may be made of a metal material and the second segment may be made of a biodegradable material such that, after the vascular prosthesis is implanted, one segment may dissolve over time, converting the vascular prosthesis into a plurality of segments, for example, at the Y-shaped branching of a bifurcated vessel. Segments also may include side-branch apertures for use in treating bifurcated vessels, graft covered segments for excluding aneurysms and drug-eluting segments that are pre-loaded with a predetermined amount of drug and may be assembled to provide a desired dose. For example, whereas metallic radially expandable inner segments provide increased radial stiffness in the deployed configuration, bio-absorbable or drug-eluting radially expandable segments may be better suited for drug delivery.

In the embodiment of FIG. 25, it is demonstrated how the interlocking mechanism of this embodiment can be employed to assemble a vascular prosthesis having variable traits along its length. Vascular prosthesis 280 includes several relatively low radial force or strength inner modular segments which form a section of relatively low radial force, strength or rigidity 282 disposed between two relatively high radial force, strength or rigidity sections 284 made of modular end segments of a relatively high radial force, strength or rigidity on each end. The interlocking mechanism of this embodiment allows physicians to assemble this "soft middle" stent. This configuration is useful for example, to dislodge plaque from an artery. A stent of uniform radial force, including in the section to be pressed against a plaque deposit in an artery, may fail to dislodge the plaque when pressed against the deposit.

Alternatively, because the interlocking mechanism of this embodiment includes substantially ring-shaped male element 182 and round female element 180 that are common for all segments, the segments may be assembled in any order desired for a specific patient or application. Thus, for example, the segments forming the relatively low radial force or strength middle section 282 may be reordered so that the low radial force segments are at one end of the stent instead of in the middle. Of course, as would be appreciated by those of skill in the art, many other combinations of materials are possible without departing from the scope of the invention.

The embodiments depicted in FIGS. 18-25 have been described hereinbefore with reference to a mechanical interlocking of the various segments of the prosthesis, by which the male and female interface elements become mutually engaged because of the physical shapes of such interlocking elements. It should be noted, however, that the male and female interlocking elements may be affixed one to the other with other techniques as well, for example, by bonding or welding the male and female interlocking elements.

Figure 26:
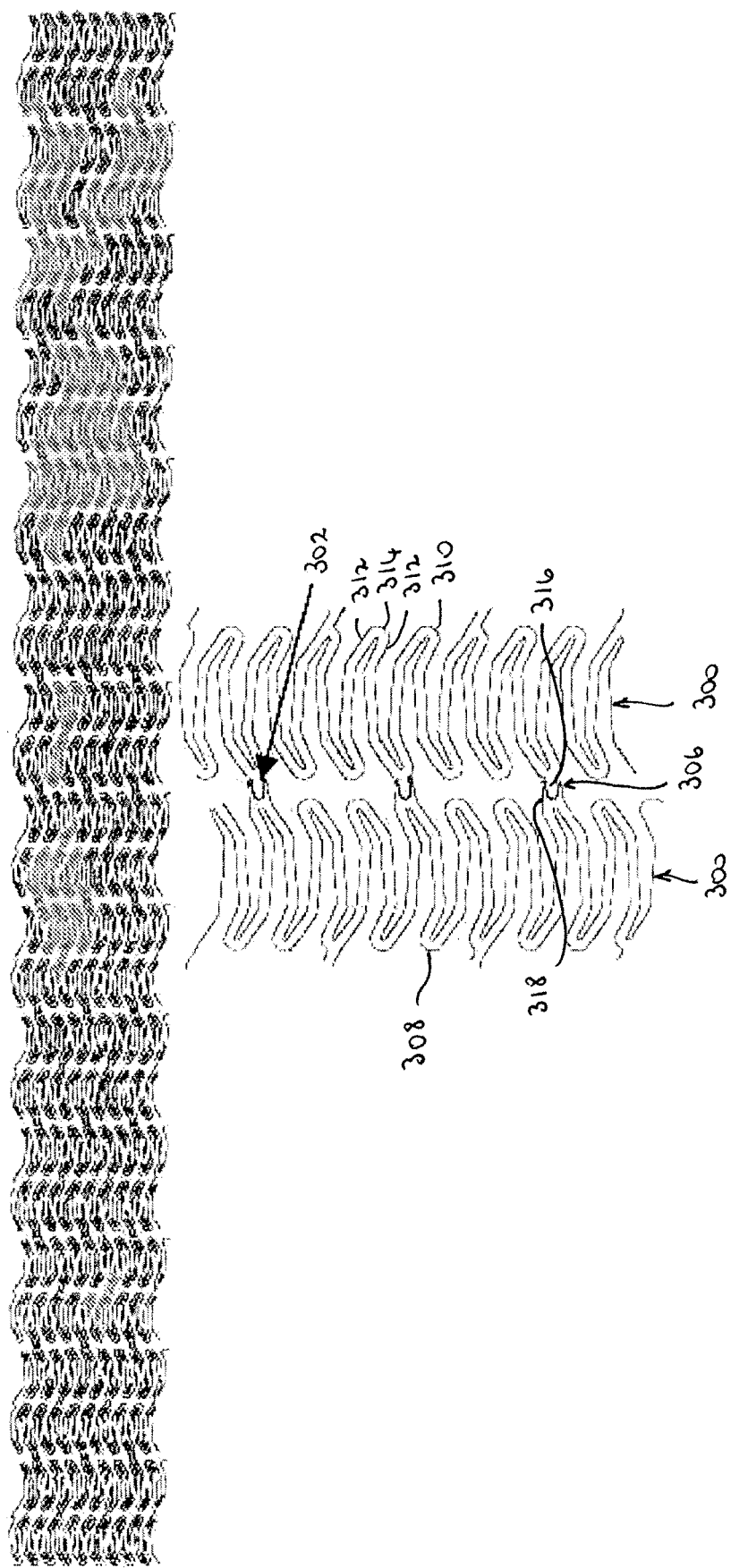
FIG. 26 is a plan view of modular segments that have been welded together and include welding zones at the connector areas.

It should further be noted that the male and female interlocking elements depicted in FIGS. 18-25 are shown as having only some of numerous possible interlocking configurations. For example, FIG. 26 illustrates an embodiment of the invention, shown in a flattened view and in a detail view, in which modular segments 300 are connected at welding zones 302 and 304 in connector areas 306 that are shaped differently from the embodiments of FIGS. 18-25. A prosthesis segment having a proximal end 308 and a distal end 310 includes a plurality of struts 312 and bends 314, but, as would be understood by one of ordinary skill in the art, interlocking modular segment 300 may include alternative strut configurations. Rounded protrusions 316 are formed on selected bends disposed between struts. Tongs 318 are formed on different selected bends disposed between struts. At welding zones 302, 304 the rounded protrusion 316 on one segment joins and inter-engages with the tongs 318 on an adjoining segment at a connector area 306 of the device. The welding zones, and ultimately the connector areas, can be formed at every third bend, as shown in FIG. 26, or it can be at every second bend, every fourth bend or other variations known to those of skill in the art depending on the particular use of the medical device. An inner segment of this embodiment might have at least one welding zone including a rounded protrusion at one end of the segment and at least one welding zone including tongs at the other end of the segment. Segments that form the ends of the device would generally have at least one welding zone including either a rounded protrusion or tongs at one end of the segment and bends without a protrusion or tongs at the other end of the segment. This is because end segments do not need to inter-engage with other segments at one of their ends.

Medical devices can be customized using this embodiment by mixing segments with different material properties, e.g., austenite finish temperatures, radial force, wall thickness or diameter, to assemble a device with specialized configurations for specific patients or applications. Moreover, this embodiment is particularly advantageous for production of long stents (e.g., 80, 100, 102 mm or longer) or stents used in smaller areas of the body, which are becoming more common for new applications such as critical limb ischemia or below-the-knee applications. This is because longer stents have a high scrap rate during laser cutting and expansion, and the connector areas and welding zones of this embodiment allow manufacturers to cut short segments and then weld the device together as a cost efficient alternative to traditional manufacturing methods.

Referring now to FIG. 11, a second family of embodiments of a vascular prosthesis constructed in accordance with the principles of the present invention is described. Vascular prosthesis 110, for example, a stent, is shown cut along line A'-A' along its longitudinal axis and flattened into a plane for illustrative purposes. As in the first family of embodiments, vascular prosthesis 110 includes a tube-like structure made up of a plurality of interconnected modular segments, including inner segments 111 and end segments 112.

Segments 111 and 112 include a plurality of struts 113 joined at the ends by bends 114 to form a generally zig-zag configuration in the deployed configuration. As would be understood by one of ordinary skill in the art, segments 111 and 112 may include many alternative strut configurations without departing from the scope of the present invention.

Figure 13:
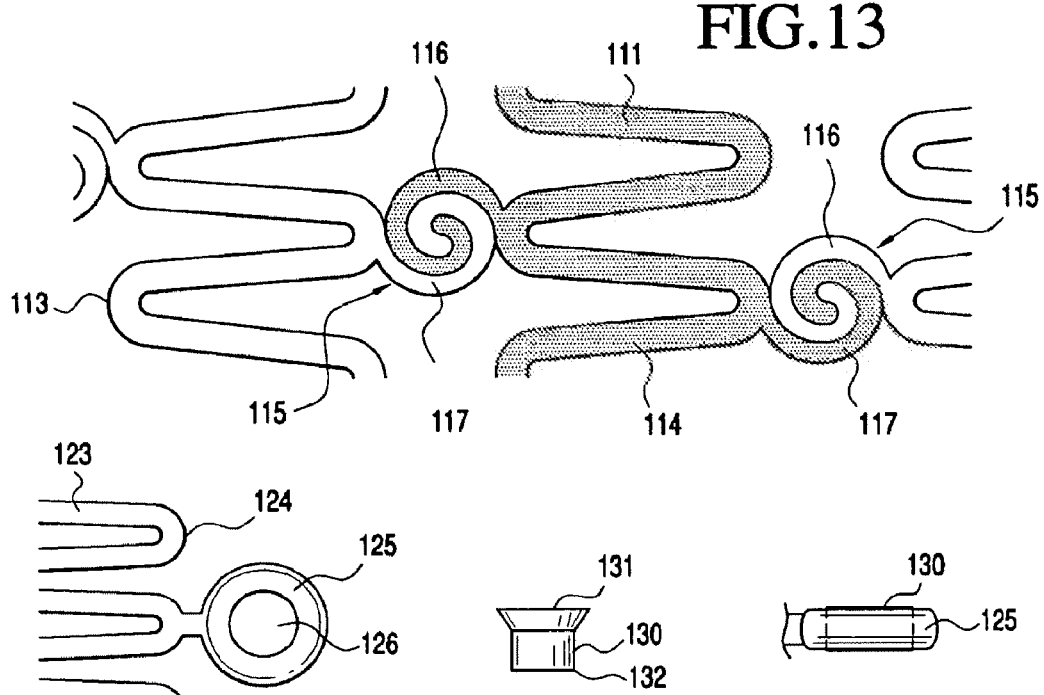
FIG. 13 is a detailed view of the intertwined spiral elements of the embodiment of FIG. 1.

Referring now also to the enlarged depiction of FIG. 13, joints 115 interconnect segments 111 and 112. Each joint 115 includes intertwined spiral elements 116 and 117, wherein elements 116 and 117 have a common orientation, either clockwise or counterclockwise, that enables the elements to intertwine. Inner segments 111 include spiral elements 116 and 117 at either end, while end segments 112 include such elements on only one end. Spiral elements 116 and 117 preferably are formed as extensions on selected bends 114 disposed between struts 113 around the circumference of the stent. Illustratively, alternating segments in FIGS. 11 and 13 are shaded for purposes of delineating the shapes of spiral elements 116 and 117, and the segments may include the same or different materials.

In FIGS. 11 and 13, spiral elements 116 are disposed on one end of each inner segment 111 and open downwards, whereas spiral elements 117 are disposed on the other end of the segment and open upwards. As will be apparent from inspection, the relative positions of spiral elements 116 and 117 may be interchanged by flipping the segment 180 degrees relative to the longitudinal axis of the prosthesis. Adjacent spiral elements are depicted as having one intervening bend 114 around the circumference of the stent, but may include two or more intervening bends. Joints 115 permit a significant degree of articulation between adjacent segments, particularly in the delivery configuration, making the stent highly flexible and thus able to negotiate tortuous anatomy.

As noted with respect to the embodiments of FIGS. 1-10, the zig-zag configuration of struts 113 and bends 114 depicted in FIG. 11 preferably is formed by laser cutting a solid tube. Vascular prosthesis 110 preferably is flexible enough to conform to the shape of a delicate vessel without substantially remodeling the vessel. In particular, the zig-zag configuration of segments 111 and 112 is expected to conform to a natural curvature of a vessel wall. Of course, other patterns of struts and bends, such as are known in the art, advantageously be used within segments 111 and 112.

Referring to FIG. 12A, vascular prosthesis 110 includes a balloon expandable material and is shown crimped in a contracted delivery configuration over balloon 120 of a balloon catheter. This may be accomplished by assembling a desired number of inner segments 111 between end segments 112 to provide a stent of a desired length, and the assembled stent may then be crimped onto balloon 120 using any of a number of previously-known crimping devices. Because the stent is retained centered on balloon 120, spiral elements 116 and 117 remain in engagement to form a substantially smooth exterior surface of the stent.

The balloon catheter carrying the stent of FIG. 12 may be delivered transluminally to a target site within a patient's vessel using well-known techniques. Joints 115 permit vascular prosthesis 110 to flex along its length to negotiate tortuous anatomy. Vascular prosthesis 110 or portions of the catheter may be radiopaque to facilitate positioning within the vessel. The target site may, for example, include a stenosed region of the vessel at which an angioplasty procedure has been conducted.

Referring to FIG. 12B, balloon 120 is inflated to expand vascular prosthesis 110 to the deployed configuration in which it engages and supports the wall of the vessel at the target site. As shown in FIG. 12B, spiral elements 116 continue to be retained in spiral elements 117 when segments 111 and 112 are radially expanded. Balloon 120 is then deflated and the balloon catheter is removed from the vessel, leaving vascular prosthesis 110 supporting the vessel. The web structure of vascular prosthesis 110 provides sufficient radial stiffness to maintain vascular prosthesis 110 in the expanded configuration, with minimal recoil. Vascular prosthesis 10 optionally may include an external coating configured to inhibit restenosis.

As for the embodiments of FIGS. 1-10, inner segments 111 of the embodiments of FIGS. 11-13 may include different materials, strut configurations, or types of radially expandable segments that are selectively intermixed to customize the vascular prosthesis for a specific patient or application. Segments also may include side-branch apertures for use in treating bifurcated vessels, graft covered segments for excluding aneurysms and drug-eluting segments that are pre-loaded with a predetermined amount of drug and may be assembled to provide a desired dose, such as described hereabove.

For example, whereas metallic radially expandable inner segments provide increased radial stiffness in the deployed configuration, bioabsorbable or drug-eluting radially expandable segments may be better suited for drug delivery. Vascular prosthesis 110 therefore may include four metallic segments alternating with four drug-eluting segments, illustratively corresponding to the shaded and unshaded segments in FIG. 11.

Because joints 115 are common for all segments of the prosthesis 110, the segments may be assembled in any order desired for a specific patient or application. Thus, for example, the segments may be reordered so that the four metallic segments are at one end of the stent, and the four polymeric segments are at the other end. Of course, as would be appreciated by those of skill in the art, many other combinations of materials are possible without departing from the scope of the invention.

Figures 14A, 14B, 14C:
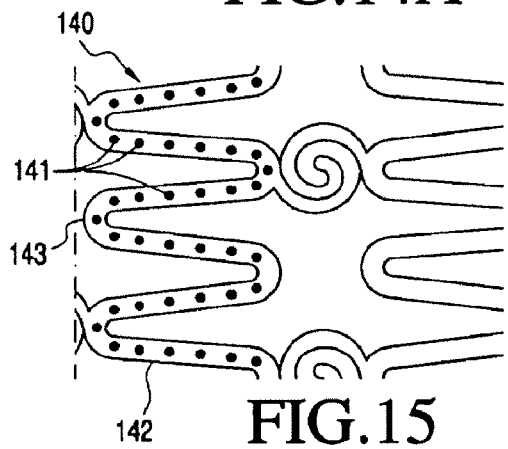
FIG. 14A-14C are, respectively, views of a marker opening and radio-opaque rivet as may be applied on the end loops of the prostheses depicted in FIGS. 1 and 11.

Referring now to FIGS. 14A to 14C, a first approach to providing a radio-opaque marker on any of the prostheses of FIGS. 1-12 is described. In FIG. 14A, struts 123 (corresponding to struts 13 of FIG. 1 or struts 113 of FIG. 11) are connected by bends 124 (corresponding to bends 14 of FIG. 1 or bends 114 of FIG. 11). In accordance with this aspect of the present invention, selected bends 124 on either or both end segments (segment 12 in FIG. 1; segment 112 in FIG. 11) include marker housings 125, in which a radiopaque marker may be disposed. Preferably, marker housings 125 are designed such that the mechanical properties of the bend of the prosthesis are not affected. Alternatively, marker housings 125 may be configured such that the marker housings function as a structural member of the prosthesis.

As shown in FIG. 14A, marker housing 125 includes aperture 126 formed therein, wherein the aperture has a generally circular shape. As will be understood, aperture 126 may be formed having other shapes, such as rectangular, square, oval, octagonal, and the like. A radio-opaque marker may be disposed within aperture 126 of marker housing 125, and may include any material having greater radio-opacity than the material from which the prosthesis is constructed. Examples of suitable material include, stainless steel, gold, silver, cobalt, platinum, iridium, tantalum, and alloys thereof or similar biocompatible or bioabsorbable materials. In a preferred embodiment, the marker includes tantalum.

As shown in FIG. 14B, the marker may be embodied in the form of rivet 130 having a generally cylindrical shape and first end 131 and second end 132. Rivet 130 may be manufactured as a composite, wherein one material may be radiopaque and the other material may be a therapeutic agent, e.g., a drug that elutes from the marker after implantation. In this case, rivet 130 may include a biocompatible material, such as described above.

Still referring to FIG. 14B, first end 131 of rivet 130 may have an enlarged diameter configured to retain the rivet within aperture 126 of marker housing 125 prior to deformation of second end 132 of the rivet. FIG. 14C depicts marker housing 125 in which rivet 130 has been disposed and second end 132 of the rivet has been deformed to lock the rivet into engagement with the marker housing.

Rivet 130 alternatively may be constructed of multiple pieces that may then be assembled to form a single member when disposed within a marker housing in accordance with the present invention. For example, the rivet may include upper, middle, and lower pieces, wherein the middle piece includes means to affix the upper and lower pieces thereto, such as a protrusion extending from each end of the middle piece, wherein the upper and lower pieces include an aperture or recessed area configured to receive the protrusion. Alternatively, a fourth piece may be utilized to affix the upper, middle and lower pieces together to form a marker in accordance with the present invention.

The rivet may be manufactured from a sheet of material, wherein the rivets are produced by stamping and a second process is performed to form the enlarged diameter section. Alternatively, the rivets may be manufactured by cutting the rivets from round stock, wherein the cut portions may then be tumbled to radius the edges then machined to produce the increased radius portion. Further still, the rivets may be manufactured utilizing other known techniques such as injection molding, casting, machining, hydroforming and the like.

Alternatively, the marker may be integrally formed with the prosthesis device during manufacturing. Such a process would involve manipulating a tubular member or a sheet of material from which the prosthesis is constructed prior to the formation of the prosthesis. For example, if the prosthesis were to be formed from a thin-walled tubular member, a groove or other feature may be formed in one of the walls of the tube, and a radio-opaque material then disposed within the groove or feature. Alternatively, the locations of the marker housing may be pre-formed on the device and the markers may pre-disposed within the marker housings prior to the manufacture of the prosthesis device, which may then be constructed according to known methods.

Figures 15, 16:
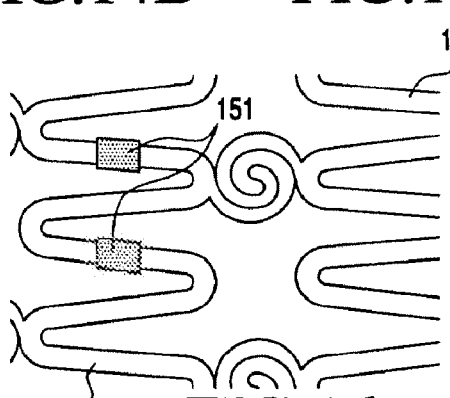
FIG. 15 is an alternative arrangement for providing radio-opaque markers on the prosthesis of the present invention.
FIG. 16 is another alternative arrangement for providing radio-opaque markers on the prosthesis of the present invention.

Referring to FIG. 15, an alternative approach to providing radio-opaque markers on the prosthesis of the present invention is described. Prosthesis 140, illustratively of the type described with respect to FIG. 11, includes a plurality of markers 141 disposed along at least one of struts 142 and bends 143. Markers 141 may include rivets disposed within openings formed in the strut members as described above or alternatively, the markers may be integrally formed upon the strut member during fabrication of the prosthesis.

For example, the prosthesis may be formed from a tubular member, wherein the struts and bends are formed in the tubular member utilizing laser cutting or similar processes. Markers 141 may be formed on the struts 142 and bends 143 by cutting away, machining away, chemical milling, or electropolishing material away from the struts to form markers 141. Although markers 141 are illustratively depicted as round in FIG. 15, the markers may be formed having any shape or profile.

In FIG. 16, a further alternative approach to providing radio-opaque markers on the prosthesis of the present invention is described. Prosthesis 150, illustratively of the type described with respect to FIG. 11, includes a plurality of markers 151 disposed along at least one of struts 152. Markers 151 include a clip or a band that may be attached to struts 152, and may be constructed of a material such as tantalum, gold, gold plating, silver, silver plating, alloyed metals, polymers, plastics, or similar biocompatible or bioabsorbable materials. Markers 152 may be configured to be retained on the prosthesis by deforming the marker such that the marker is frictionally retained on the prosthesis. Alternatively, markers 152 may be affixed to the prosthesis utilizing other methods such as welding, gluing, swaging, or similar methods.

It is contemplated that the markers described above may be formed anywhere along the length of the prosthesis. For example, it is contemplated that marker housings or markers may be formed for example in the middle of the prosthesis to indicate a specific area or property of the prosthesis. As such, markers may be disposed in marker housings formed within the struts or bends of the prosthesis, or integrated in the prosthesis anywhere along the length of the prosthesis. Further still, a variety of the marker embodiments described and shown herein may be utilized in any combination along the length of an prosthesis according to the present invention, wherein different marker embodiments may be utilized to mark locations of interest.

Figure 17:
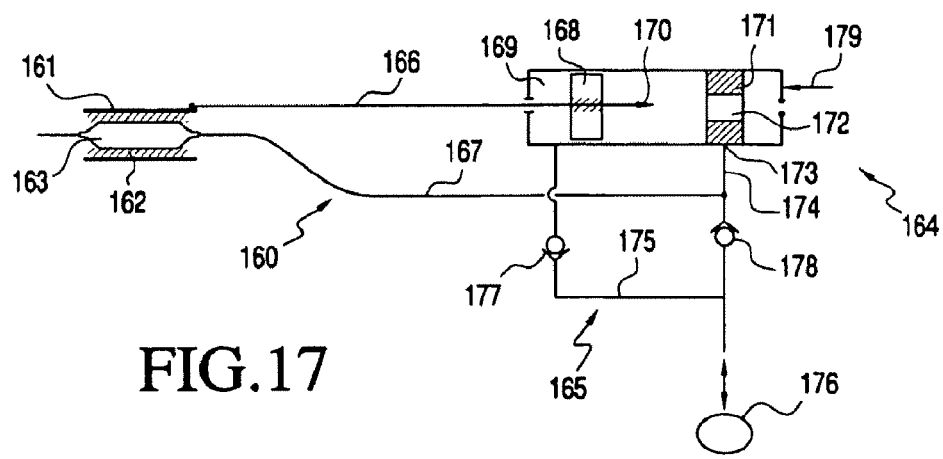
FIG. 17 is an illustrative delivery system for use in delivering the prosthesis of the present invention.

Referring now to FIG. 17, an illustrative delivery system for use with the prostheses of the present invention is described, such as described in greater detail in International Patent Publication No. WO 2004/014256. That publication is incorporated herein by reference in its entirety. More particularly, delivery system 160 includes sheath 161 is arranged on stent 162 supported by balloon 163. Sheath 161, stent 162 and balloon 163 are supported by a catheter (not shown), which may be inserted into a patient's vasculature. Sheath retraction device 164 and fluid pressure 165 are connected with the delivery system 160 by wire 166 and tube 167, respectively.

Wire 164 connects sheath 161 with piston 168 in cylinder 169. Hook 170 is disposed from the proximal side of piston 168. Cylinder 169 further includes floating second piston 171 with opening 172 that can be penetrated by hook 170. Floating piston 171 closes outlet 173 in cylinder 169. Tube 167 connects balloon 163 with tube 174 mounted at outlet 173 of cylinder 169. Tube 175 is connected to a inflation/deflation device schematically shown as double-arrow 176 at the one end and via a unidirectional valve (check valve) 177 with cylinder 169 at the other end. Furthermore, tube 175 is connected via a unidirectional valve (check valve) 178 with tube 167.

Operation of delivery system 160 is as follows: Balloon 163 is in a deflated state and sheath 161 covers stent 162. Floating second piston 171 is positioned so that outlet 173 of cylinder 169 and, thus tube 174, are closed. A clinician applies pressure from inflation/deflation device 176 to tube 175. The pressure shuts unidirectional valve 178 and opens unidirectional valve 177. This causes pressurized fluid to flow into cylinder 169 and shifts first piston 168 in the proximal direction, thereby retracting wire 166 and sheath 161 from stent 162. The delivery system is designed so that the pressure required to move piston 168 is very low.

When first piston 168 reaches floating second piston 171, the proximal end of wire 166 with hook 170 penetrates opening 172 in piston 171, and piston 168 moves piston 171 to the proximal end of cylinder 169. Hook 170 engages hook holder 179, wherein piston 168 with wire 166 and sheath 161 is fixed at the proximal end. In this position, sheath 161 is completely retracted from stent 162, and outlet 173 of cylinder 169 is open. In this manner, the pressurized fluid from the inflation/deflation device 176 flows via tube 175 and the left side of cylinder 169 through outlet 173, tube 174 and tube 167 to balloon 163, and inflates the balloon to deploy stent 162. The pressure may be applied until a desired expanded diameter is attained for the prosthesis.

Once the prosthesis is deployed, the clinician applies a vacuum from the inflation/deflation device 176 via unidirectional valve 178 and tube 166 to balloon 163. During this suction step, unidirectional valve 177 is closed. At the end of the stent delivery and deployment process, the catheter with balloon 163 and sheath 161 is removed from the patient's vessel, leaving the prosthesis in the desired position within the vessel.

It is to be understood that the foregoing delivery system is merely illustrative of the types of delivery systems that may be used to deliver and deploy the prostheses of the present invention. Alternatively, a delivery system such as described in co-pending, commonly assigned U.S. patent application Ser. No. 10/932,964, filed Sep. 2, 2004, and entitled "Delivery System for a Medical Device," which is incorporated herein by reference, may be employed It should be understood that any of the foregoing joint configurations and specialized modular segments may be interchangeably used with any of the vascular prostheses of the preceding embodiments. In this manner, the methods and apparatus of the present invention permit a vascular prosthesis to be tailored to a given patients anatomy or a specific application.

Although preferred illustrative embodiments of the present invention are described hereinabove, it will be evident to one skilled in the art that various changes and modifications may be made therein without departing from the invention. It is intended in the appended claims to cover all such changes and modifications that fall within the true spirit and scope of the invention.

What is claimed is:

1. A method of assembling a modular prosthesis comprising:
   providing a plurality of interlocking modular segments, wherein each interlocking modular segment has a proximal and a distal end, a plurality of struts and a plurality of bends disposed between the proximal and distal ends, a ring shaped male interface element at the proximal end of the module, and a rounded female interface element at the distal end of the module; and
   joining the plurality of interlocking modular segments by inserting the ring shaped male interface element at the proximal end of one interlocking modular segment into the rounded female interface element at the distal end of another interlocking modular segment, the plurality of interlocking module segments being joined together in a delivery configuration and a deployed configuration.

2. The method of claim 1, wherein the one and the another interlocking modular segments fixedly engage one another, thereby causing the interlocking modular segments not to move axially relative to one another.

3. The method of claim 2, wherein the one and the another interlocking modular segments fixedly engage each other by mechanically interlocking, by bonding or by welding the one and the another interlocking modular segments to one another.

4. The method of claim 1, wherein each ring shaped male interface element and/or each rounded female interface element comprises an extension of a corresponding one of the plurality of struts.

5. The method of claim 1, further comprising providing at least two interlocking modular segments having different lengths.

6. The method of claim 1, further comprising providing at least two interlocking modular segments made of different materials.

7. The method of claim 6, wherein one of the different materials is biodegradable.

8. The method of claim 6, wherein the different materials possess different mechanical properties.

9. The modular vascular prosthesis of claim 1, wherein the one and the another interlocking modular segments have different strut configurations.

10. The method of claim 1, wherein the one interlocking modular segment is balloon expandable and the another interlocking modular segment is self-expanding.

11. The method of claim 1, wherein at least one of the one or another interlocking modular segments comprises a drug-eluting polymeric material.

12. The method of claim 1, wherein at least one of the one or another interlocking modular segments includes a side-branch aperture.

13. The method of claim 1, wherein at least one of the one or another interlocking modular segments includes a cover comprising a biocompatible graft material.

14. The method of claim 1, further comprising:
   another plurality of interlocking modular segments extending from the distal end of the one interlocking modular segment, individual ones of the plurality of interlocking modular segments interleaved with individual ones of the one interlocking modular segment; and
   an additional plurality of interlocking modular segments extending from the proximal end of the another interlocking modular segment, individual ones of the plurality of interlocking modular segments interleaved with individual ones of the another interlocking modular segment.

15. A modular vascular prosthesis having a delivery configuration and a deployed configuration, the modular vascular prosthesis comprising:
   a plurality of interlocking modular segments each having a proximal end and a distal end, and a plurality of struts and bends therebetween,
   wherein each of the plurality of interlocking modular segments further has a ring shaped male interface element at the proximal end and a rounded, open-ended female interface element at the distal end, each rounded, open-ended female interface element being disposed at the end of a single strut of the plurality of struts, the cooperating ring shaped male interface element of one interlocking modular segment and rounded, open-ended female interface element of another interlocking modular segment interlocking both in a delivery configuration and a deployed configuration.

16. The modular vascular prosthesis of claim 15, further comprising:
   a first interlocking modular end segment having a proximal and a distal ends, a plurality of struts and a plurality of bends at the proximal end, and a rounded female interface element at the distal end;
   a second interlocking modular end segment having a proximal and distal ends, a plurality of struts and a plurality of bends at the distal end, and a ring shaped male interface element at the proximal end;
   wherein the plurality of interlocking modular segments are joined to each other by inserting the ring shaped male interface element at the proximal end of a first interlocking modular segment of the plurality of interlocking modular segments into the rounded female interface element at the distal end of a second interlocking modular segment of the plurality of interlocking modular segment;
   wherein at least one of the plurality of interlocking modular segments is joined to the first interlocking modular end segment by inserting the ring shaped male interface element at the proximal end of the interlocking modular segment to the rounded female interface element at the distal end of the first interlocking modular end segment; and
   wherein at least one of the plurality of interlocking modular segments is joined to the second interlocking modular end segment by inserting the ring shaped male interface element at the proximal end of the interlocking modular end segment to the rounded female interface element at the distal end of the interlocking modular segment.

17. The modular vascular prosthesis of claim 16, wherein at least two interlocking modular segments of the plurality of interlocking module segments have different lengths.

18. The modular vascular prosthesis of claim 16, wherein at least two interlocking modular segments of the plurality of interlocking module segments are made of different materials.

19. The system of claim 18, wherein one of the different materials is biodegradable.

20. The system of claim 18, wherein the different materials possess different mechanical properties.

21. The system of claim 18, wherein the plurality of struts and bends has an angled branch configuration.

22. A vascular prosthesis having a delivery configuration and a deployed configuration, the vascular prosthesis comprising:
   a first modular segment and a second modular segment, each of the first modular segment and the second modular segment having a proximal end and a distal end, and a plurality of struts and bends therebetween,
   wherein each of the first modular segment and the second modular segment has at least one ring shaped male interface element formed on at least one selected strut of the plurality of struts, and at least one rounded, open-ended female interface formed on at least one selected strut of the plurality of struts, each ring shaped male interface and each rounded, open-ended female interface being disposed at the end of a single strut of the plurality of struts, the cooperating ring shaped male interface element of the first modular segment and the rounded, open-ended female interface element of the second modular segment interlocking both in a delivery configuration and a deployed configuration.

23. The vascular prosthesis of claim 22, wherein the plurality of struts are disposed in an angled branch configuration.

24. The vascular prosthesis of claim 22, wherein the first and the second modular segments have different lengths.

25. The vascular prosthesis of claim 22, wherein the first and the second modular segments are made of different materials.

26. The vascular prosthesis of claim 22, wherein the first and the second modular segments possess different mechanical properties.

* * * * *